United States Patent [19]

Enomoto et al.

[11] Patent Number: 5,106,860
[45] Date of Patent: * Apr. 21, 1992

[54] THIAZOLIDIN-4-ONE DERIVATIVES AND ACID ADDITION SALTS THEREOF USEFUL FOR TREATING PAF MEDIATED DISEASES

[75] Inventors: Masao Enomoto, Osaka; Atsuyuki Kojima, Takarazuka; Yoshihiro Komuro, Nishinomiya; Shigeaki Morooka, Kawanishi; Shunji Aono, Toyonaka; Yuzuru Sanemitsu, Ashiya; Masato Mizutani; You Tanabe, both of Toyonaka, all of Japan

[73] Assignee: Sumitomo Chemical Company, Limited, Osaka, Japan

[*] Notice: The portion of the term of this patent subsequent to Feb. 12, 2008 has been disclaimed.

[21] Appl. No.: 624,566

[22] Filed: Dec. 10, 1990

Related U.S. Application Data

[62] Division of Ser. No. 196,058, May 19, 1988, Pat. No. 4,992,455.

[30] Foreign Application Priority Data

| May 22, 1987 [JP] | Japan | 62-126391 |
| Jun. 2, 1987 [JP] | Japan | 62-139304 |
| Jun. 26, 1987 [JP] | Japan | 62-160481 |
| Jan. 22, 1988 [JP] | Japan | 63-12379 |

[51] Int. Cl.$^5$ .................. C07D 417/04; C07D 7/02; A61K 31/42
[52] U.S. Cl. .................. 514/342; 546/14; 546/280
[58] Field of Search .................. 546/280, 14; 514/342

[56] References Cited

U.S. PATENT DOCUMENTS

| 4,017,628 | 4/1977 | Nitidandhaprabhas et al. ... 546/280 X |
| 4,406,905 | 9/1983 | Zahner et al. .................. 514/342 |
| 4,436,739 | 3/1984 | Krumkalns .................. 514/342 X |
| 4,443,454 | 4/1984 | Worthington .................. 514/342 X |
| 4,501,746 | 2/1985 | Krumkalns .................. 514/357 |
| 5,021,435 | 6/1991 | Masai et al. .................. 514/342 |

FOREIGN PATENT DOCUMENTS

0010420 4/1980 European Pat. Off. ............ 546/280

OTHER PUBLICATIONS

Chemical Abstracts, vol. 97, No. 25, Dec. 20, 1982, p. 853, Abstract No. 216166j.
J. Am. Chem. Soc., 75, 109–114 (1953).
J. Am. Chem. Soc., 76, 578–580 (1954).
J. Am. Chem. Soc., 70, 3436–3439 (1948).

Primary Examiner—Alan L. Rotman
Attorney, Agent, or Firm—Stevens, Davis, Miller & Mosher

[57] ABSTRACT

Thiazolidin-4-one derivative represented by the following general formula (I) and acid addition salts thereof $$\underset{R^2}{\overset{R^1}{\diagdown}}\!\!\!\diagup\!\!\!\!\underset{O}{\overset{S}{\diagdown}}\!\!\!\!\diagup\!\!\!\!\underset{R^3}{\overset{N}{\diagdown}}\!\!\!\!\!\!\!\!\!\!\bigg\langle\!\!\!\!\!\!\!\!\!\!\!\overset{N}{\diagdown}\quad\text{(I)}$$

wherein;
$R^1$ and $R^2$ are the same or different and denote each
(i) a residue represented by the general formula $$-A-R^4$$

wherein, A denotes a single bond, $C_1$–$C_8$ alkylene, $C_2$–$C_8$ alkenylene, or $C_2$–$C_8$ alkynylene and $R^4$ denotes hydrogen, $C_1$–$C_{12}$ alkyl, $C_2$–$C_8$ alkenyl, $C_3$–$C_8$ cycloalkyl, or $C_1$–$C_6$ haloalkyl, or (ii) a residue represented by the general formula $$\{(CH_2)_{\overline{n}}O\}_{\overline{m}}\{(CH_2)_{\overline{n'}}O\}_{\overline{m'}}-B-R^5$$

wherein, B denotes a single bond or $C_1$–$C_6$ alkylene, $R^5$ denotes hydrogen, $C_1$–$C_6$ alkyl, $C_2$–$C_8$ alkenyl, $C_3$–$C_8$ cycloalkyl, substituted silyl, or substituted or unsubstituted aryl, n and n' denote each an integer of 2 to 4, m denotes an integer of 1 to 3, and m' denotes an integer of 0 to 2;

$R^3$ denotes hydrogen, $C_1$–$C_2$ alkyl, allyl, 2-propynyl, or (c) the general formula $$-F-R^9$$

wherein, F denotes $C_2$–$C_6$ alkylene and $R^9$ denotes a nitrogen-containing heterocyclic aromatic residue or an amino group represented by the general formula $$-N\!\!\diagup\!\!\overset{R^{11}}{\diagdown}\!\!\!\!\!\underset{R^{10}}{}$$

($R^{10}$ denotes hydrogen, $C_2$–$C_4$ alkyl or $C_1$–$C_4$ alkanoyl and $R^{11}$ denotes hydrogen or $C_1$–$C_4$ alkyl or $R^{10}$ in combination with $R^{11}$ denotes a 5- to 7-membered cyclic amino group which optionally contains other hetero atoms.

Having selective PAF-antagonistic activities, these compounds are very useful as preventive and curative agents for PAF-induced diseases, for example, various kinds of inflammation, allergic diseases, circulatory diseases, and gastro-intestinal diseases.

12 Claims, No Drawings

THIAZOLIDIN-4-ONE DERIVATIVES AND ACID ADDITION SALTS THEREOF USEFUL FOR TREATING PAF MEDIATED DISEASES

This is a division of application Ser. No. 07/196,058, filed May 19, 1988, U.S. Pat. No. 4,992,455 issued Feb. 12, 1991.

BACKGROUND OF THE INVENTION

1. Field of the Invention

The present invention relates to novel 2-pyridyl-tiazolidin-4-one derivatives which shown excellent antagonisms to the platelet activating factor (hereinafter abbreviated as PAF).

2. Description of the Prior Art

PAF is a factor which in minute amounts can activate rabbit blood platelets. This factor was found in the supernatant of a culture of antigen-stimulated basophils of IgE-sensitized rabbits [Benveniate, J. et al J.P. Med., 136, 1356-1377 (1972)]. PAF is autocoid present in living bodies which has been identified as acetyl glyceryl ether phosphorylcholine (AGEPC), i.e. 1-O-hexadecyl-/octadecyl-2-o-acetyl-sn-glyceryl-3-phosphorylcholine [Hanahan, D. J. et al., J. Biol. Chem, 254, 9355-9385 (1979)].

It is known that in addition to the platelet activation, PAF in extremely low concentrations exhibits various physiological actions, e.g. the depression of blood pressure, increase in vascular permeability, contraction of smooth muscle, activations of leucocyte-, monocyte-, and macrophage, and acceleration of liver glycogen decomposition.

These physiological actions are regarded as being associated with a number of diseases, e.g. various kinds of inflammation, allergic diseases, circulatory diseases, and gastrointestinal diseases. Accordingly, the search of PAF-antagonists has been focused and energetically conducted in recent years for the purpose of preventing and/or treating these PAF-induced diseases.

However, while several compounds have been tested up to now to treat or prevent PAF-induced diseases, their effectiveness are not fully satisfactory.

On the other hand, a great number of studies are reported which relate to thiagolidin-4-one derivatives. Of these studies, however, those relating to 2-pyridyl-thiazolidin-4-one derivatives are reported only by the following seven documents: Japanese Patent Application Kokai (Laid-Open) No. 145670/79 discloses N-(substituted or unsubstituted phenyl and pyridyl) derivatives of 2-pyridylthiazolidin-4-one which are useful as agricultural chemicals. Japanese Patent Application Kokai No. 55184/80 discloses compounds including chiefly N-(substituted or unsubstituted phenyl, benzyl, and cycloalkyl) derivatives of 2-pyridylthiazolidin-4-one which are useful as agricultural chemicals. Japanese Patent Application Kokai Nos. 85380/82 and 88170/82 discloses the N-carboxycyclohexylmethyl derivatives of 2-pyridylthiazolidin-4-one and the N-carboxymethylphenyl derivatives of the same compounds respectively, the former having an anti-complementary activity and the latter having antiinflammatory, analgesic, and antirheumatic activities. Japanese Patent Application Kokai No. 183689/83 discloses the N-pyrazinyl derivative of 2-pyridylthiazolidin-4-one useful as an agricultural chemical. U.S. Pat. No. 4,501,746 discloses N-(substituted phenyl) derivatives of 2-pyridylthiazolidin-4-one which are useful as intermediates in syntheses.

Further, Japanese Patent Application Kokai No. 103881/86 disclosed N-(substituted carbamoyloxy) derivatives of 2-pyridylthazolidin-4-one which are useful as cardiotonica.

SUMMARY OF THE INVENTION

Under such circumstances as stated above, the present inventors made intensive studies with the object of searching out a useful PAF-antagonistic agent. As a result, it has been found that thiazolidin-4-one derivatives represented by the following general formula [I] and acid addition salts thereof have selective PAF-anatagonistic activities and are very useful therapeutic agents for preventing and/or treating PAF-induced diseases, for example, various kinds of inflammation, allergic diseases, circulatory diseases, and gastrointestinal diseases.

General formula [I]

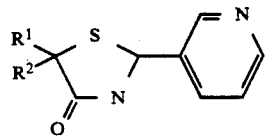

wherein
$R^1$ and $R^2$ are the same or different and denote each
(i) a residue represented by the general formula $$-A-R^4$$

wherein, A denotes a single bond, $C_1-C_8$ alkylene, $C_2-C_8$ alkenylene, or $C_2-C_8$ alkynylene and $R^4$ denotes hydrogen, $C_1-C_{12}$ alkyl, $C_2-C_8$ alkynyl, $C_3-C_8$ cycloalkyl, or $C_1-C_6$ haloalkyl, or (ii) a residue represented by the general formula $$\{(CH_2)_n O\}_m\{(CH_2)_{n'} O\}_{m'} B-R^5$$

wherein, B denotes a single bond or $C_1-C_6$ alkylene, $R^5$ denotes hydrogen, $C_1-C_6$ alkyl, $C_2-C_8$ alkenyl, $C_3-C_8$ cycloalkyl, substituted silyl, or substituted or unsubstituted aryl, n and n' denote each an integer of 2 to 4, m denotes an integer of 1 to 3, and m' denotes an integer of 0 to 2; and
$R^3$ denotes hydrogen, $C_1-C_2$ alkyl, allyl, 2-propynyl, or a residue represented by (a) the general formula $$+CH_2\}_l R^6$$

wherein, $R^6$ denotes halogen, an aryl group substituted or unsubstituted by one or more hydroxy or $C_1-C_4$ alkoxy groups, or a residue represented by the general formula $-D-R^7$ (D denotes oxygen or sulfur and $R^7$ denotes hydrogen, $C_1-C_4$ alkyl, or $C_1-C_4$ alkanoyl) and l denotes an integer of 2 to 4, $$+CH_2\}_k CO-E-R^8$$

wherein, E denotes oxygen, sulfur, imino, or $C_1-C_4$ alkylimino, $R^8$ denotes hydrogen, or $C_1-C_4$ alkyl, or $-(E-R^8)$ denotes a 5- to 7-membered cyclic amino group which optionally contains other hetero atoms, and k denotes an integer of 1 to 3, or (c) the general formula

wherein, F denotes $C_2$-$C_6$ alkylene and $R^9$ denotes a nitrogen-containing heterocyclic aromatic residue or a residue represented by the general formula

($R^{10}$ denotes hydrogen, $C_1$-$C_4$ alkyl, or $C_1$-$C_4$ alkanoyl and $R^{11}$ denotes hydrogen or $C_1$-$C_4$ alkyl or $R^{10}$ in combination with $R^{11}$ denotes a 5- to 7-membered cyclic amino group which optionally contains other hetero atoms).

Based on this finding, the present invention has been accomplished.

DETAILED DESCRIPTION OF THE INVENTION

In this specification, the "$C_1$-$C_{12}$ alkyl" means any of linear and branched alkyl groups including, e.g. methyl, ethyl, n-propyl, n-butyl, sec-butyl, n-pentyl, isopentyl, n-hexyl, n-heptyl, n-octyl, n-nonyl, n-decyl, n-undecyl, and n-dodecyl; the "$C_2$-$C_8$ alkenyl" means any of linear and branched $C_2$-$C_8$ alkenyl groups including, e.g. vinyl, 2-propenyl, 2-butenyl, 3-methyl-2-butenyl, 2-pentenyl, 3-pentenyl, 4-pentenyl, 4-methyl-3-pentenyl, 2-hexenyl, 4-hexenyl, 5-methyl-4-hexenyl, 2-heptenyl, 6-methyl-5-heptenyl, 2-octenyl, and 6-oxtenyl; the "$C_3$-$C_8$ cycloalkyl" means any of substituted or unsubstituted $C_3$-$C_8$ cycloalkyl groups including, e.g. cyclopropyl, cyclobutyl, cyclopentyl, cyclohexyl, cycloheptyl, and 1-methyl-cyclohexyl; the "$C_1$-$C_6$ haloalkyl" means any of halogenated $C_1$-$C_6$ alkyl groups including, e.g. monofluoromethyl, difluoromethyl, trifluoromethyl, pentafluoroethyl, heptafluoropropyl, nonafluorobutyl, undecafluoropentyl, and tridecafluorohexyl; the "substituted or unsubstituted aryl" means any of substituted or unsubstituted aryl groups including, e.g. phenyl, naphthyl, p-chlorophenyl, o-chlorophenyl, p-fluorophenyl, 2,6-dichlorophenyl, p-methoxyphenyl, and 3,4-dimethoxyphenyl; the "$C_1$-$C_8$ alkylene" means any of linear and branched $C_1$-$C_8$ alkylene-groups including, e.g. methylene, ethylene, trimethylene, 1-methyltrimethylene, tetramethylene, pentamethylene, hexamethylene, and heptamethylene; the "$C_2$-$C_8$ alkenylene" means any of linear and branched $C_2$-$C_8$ alkenylene groups including, e.g. vinylene, propenylene, 2-butenbutenylene, 2-methyl-2-butenylene, 2-pentenylene, 3-pentenylene, 2-hexenylene, 3-methyl-2-hexenylene, 3-heptenylene, and 4-oxtenylene; the "$C_2$-$C_8$ alkynylene" means any of linear and branched $C_2$-$C_8$ alkynylene groups including e.g. ethynylene, propynylene, 2-butynylene, 2-methyl-2-butynylene, 2-pentynylene, 3-pentynylene, 2-hexynylene, 3-methyl-2-hexynylene, 3-heptynylene, and 4-oxtynylene; the "$C_1$-$C_6$ alkylene" means any of linear and branched $C_1$-$C_6$ alkylene groups including, e.g. methylene, ethylene, trimethylene, 1-methyltrimethylene, tetramethylene, pentamethylene, and hexamethylene; the "$C_1$-$C_6$ alkyl" means any of linear and branched $C_1$-$C_6$ alkyl groups including, e.g. methyl, ethyl, n-propyl, n-butyl, sec-butyl, n-pentyl, isopentyl, and n-hexyl; the "substituted silyl" means any of groups including, e.g. trimethylsilyl, triethylsilyl, isopropyldimethylsilyl, t-butyldimethylsilyl, methyldiisopropylsilyl, methyldi-t-butylsilyl, tribenzylphenyltriisopropylsilyl, and triphenylsilyl; the "$C_1$-$C_2$ alkyl" means methyl or ethyl; the "halogen" means a halogen atom such as fluorine, chlorine, or bromine; the "$C_1$-$C_4$ alkoxy" means any of linear and branched $C_1$-$C_4$ alkoxy groups including, e.g. methoxy, ethoxy, n-propoxy, isopropoxy, and n-butoxy; the "$C_1$-$C_4$ alkyl" means any of linear and branched $C_1$-$C_4$ alkyl groups including, e.g. methyl, ethyl, n-propyl, isopropyl, n-butyl, and isobutyl; the "$C_1$-$C_4$ alkanoyl" means any of linear and branched $C_1$-$C_4$ alkanoyl groups including, e.g. formyl, acetyl, propionyl, butyryl, and isobutyryl; the "$C_1$-$C_4$ alkylimino" means, e.g. methylimino, ethylimino, n-propylimino, or isobutylimino group; the "5- to 7-membered cyclic amino group" means, e.g. pyrrolidinyl, piperidinyl, homopiperidinyl, morpholinyl, piperazinyl, or N-methylpiperazinyl; the "$C_1$-$C_6$ alkylene" means any of linear and branched $C_1$-$C_6$ alkylene groups including, e.g. methylene, ethylene, trimethylene, 1-methyltrimethylene, tetramethylene, pentamethylene, and hexamethylene; and the "nitrogen-containing heterocyclic aromatic residue" means e.g. pyrrole, imidazole, or pyrrazole ring.

Acid addition salts of thiazolidin-4-one derivatives represented by the general formula [I] are pharmaceutically acceptable salts including; salts with mineral acids, e.g. hydrochloric acid, hydrobromic acid, sulfuric acid, and phosphoric acid; salts with organic carboxylic acids, e.g. formic acid, acetic acid, fumaric acid, maleic acid, citric acid, lactic acid, malic acid, tartaric acid, and aspartic acid; and salts with sulfonic acids, e.g. methanesulfonic acid, benzenesulfonic acid, toluenesulfonic acid, hydroxybenzenesulfonic acid, dihydroxybenzenesulfonic acid, and naphthalenesulfonic acid.

Compounds used in the invention include optical isomer, geometrical isomers, and moreover, hydrates and various crystal forms thereof.

Thiazolidin-4-one derivatives represented by the general formula [I] can be prepared, for example, by the following methods (a) to (k).

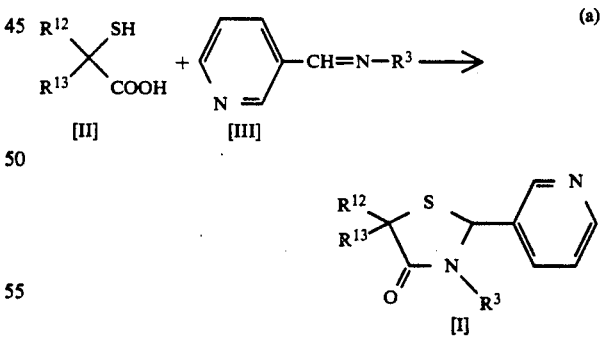

In this equation, $R^{12}$ and $R^{13}$ are the same or different and denote each a residue represented by the general formula

(wherein A and $R^4$ are as defined above) and $R^3$ is as defined above.

That is, the present inventive compound [I] can be prepared by subjecting the thioglycolic acid derivative [II] and the Schiff's base [III] to ring closure in an inert solvent. Such solvents include benzene, toluene, xylene, dichloromethane, 1,2-dichloroethane, chloroform, and tetrahydrofuran, which are commonly used as inert solvents in dehydration reactions, and mixtures of these solvents with ethanol or the like. While this reaction can be carried out at temperatures of 20° C. to the reflux temperature, it is preferable with azeotropic dehydration, thereby promoting the reaction.

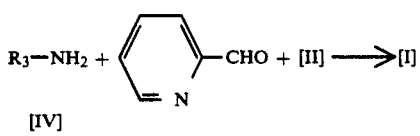

(b)

In this equation, $R^3$ is as defined above.

That is, the compound [I] can be prepared by subjecting the primary amine [IV], the compound [II], and nicotin aldehyde to ring closure in an inert solvent. Similarly to the method (a), suitable inert solvents are benzene, toluene, xylene, dichloromethane, 1,2-dichloroethane, chloroform, tetrahydrofuran, etc. and mixtures of these solvents with ethanol or the like. While this reaction can also be carried out at temperatures of 20° C. to the reflux temperature, it is preferable with azeotropic dehydration, thereby promoting the reaction.

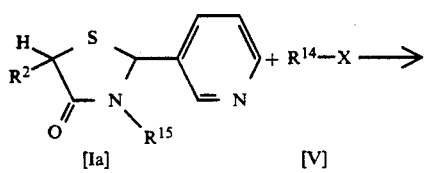

(c)

In this equation, $R^{14}$ is a residue represented by either the general formula $$-A-R^4$$

(wherein A and $R^4$ are as defined above) or the general formula

(wherein, B, $R^5$, n, n', m, and m' are as defined above) and
$R^{15}$ denotes $C_1$–$C_6$ alkyl, allyl, 2-propynyl, or a residue by (i) the general formula

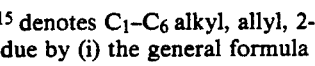

(wherein, $R^{16}$ denotes an aryl group substituted or unsubstituted by one or more $C_1$–$C_4$ alkoxy groups, or a residue represented by the general formula

(wherein, $R^{17}$ denotes $C_1$–$C_4$ alkyl and D is as defined above and l is as defined above), (ii) the general formula

(wherein, G denotes oxygen atom or $C_1$–$C_4$ alkylimino, $R^{18}$ denotes $C_1$–$C_4$ alkyl, or the G—$R^{18}$ combination denotes a 5- to 7-membered heterocyclic amino group which may or may not contain other hetero atoms, and k is as defined above), or (iii) the general formula

(wherein F and $R^9$ are as defined above),
X denotes a leaving group and $R^2$ is as defined above.

The leaving group X can be exemplified by: halogen atoms such as chlorine, bromine, and iodine; lower alkylsulfonyloxy groups such as methylsulfonyloxy and ethylsulfonyloxy; substituted or unsubstituted arylsulfonyloxy groups such as phenylsulfonyloxy and tolylsulfonyloxy; and acyloxy groups such as acetyloxy and benzoyloxy. Of these groups, preferred are halogen atoms, e.g. bromine and iodine.

That is, the compound [Ib] can be prepared by reacting the compound [V] with the compound [Ia] in the presence of a base. Suitable bases for this reaction include; organo-alkali metal compounds, e.g. butyllithium; alkali metal amides, e.g. lithium diisopropylamide; alkali metal hydrides, e.g. sodium hydride; alkali metal alkoxides, e.g. potassium tert-butoxide; and other organic bases, e.g. 1,5-diazabicyclo[4,3,0]nonane-5-ene, 1,8-diazabicyclo[5,4,0]-undecane-7-ene, N-methylmorpholine, and 4-dimethylaminopyridine. Desirably, the reaction is conducted in an inert solvent, e.g. tetrahydrofuran, dioxane, n-hexane, or toluene, at a temperature of −50° C. to the reflux temperature.

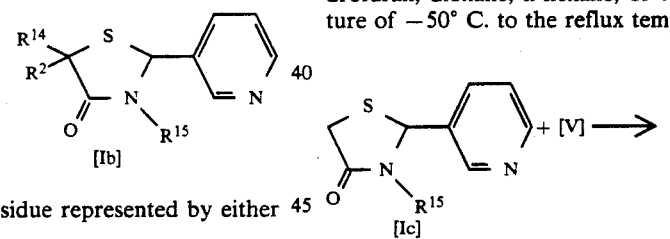

(d)

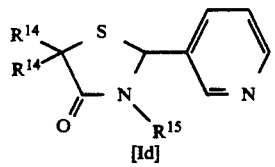

In this equation, $R^{14}$ and $R^{15}$ are as defined above.

Thus, the compound [Id] can be prepared by reacting the compound [V] with the compound [Ic] in the presence of a base. Suitable bases include; organo alkali metal compounds, e.g. butyllithium; alkali metal amides, e.g. lithium diisopropylamide; alkali metal hydrides, e.g. sodium hydride; alkali metal alkoxides, e.g. potassium tert-butoxide; and other organic bases, e.g. 1,5-diazabicyclo [4.3.0] nonane-5-ene, 1,8-diazabicyclo [5.4.0] undercane-7-ene, N-methylmorpholine, and 4-dimethylaminopyridine. Desirably, the reaction is conducted in an inert solvent, e.g. tetrahydrofuran, dioxane, n-hexane, or toluene, at a temperature of −50° C. to the reflux temperature.

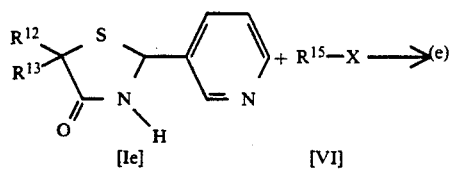

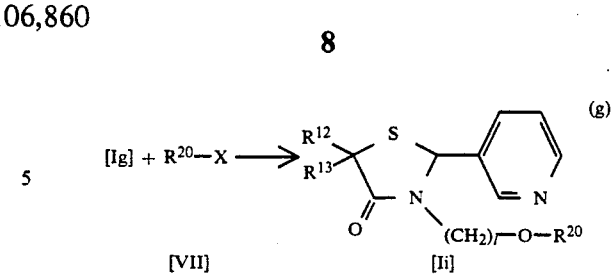

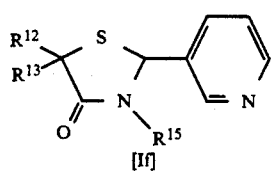

In this equation, X denotes a leaving group and $R^{12}$, $R^{13}$, and $R^{15}$ are as defined above.

Thus, the compound [If] can be prepared by reacting the compound [VI] with the compound [Ie] in the presence of a base. Suitable bases include; organo alkali metal compounds, e.g. butyllithium; alkali metal amides, e.g. lithium diisopropylamide; alkali metal hydrides, e.g. sodium hydride; alkali metal alkoxides, e.g. potassium tert-butoxide; and other organic bases, e.g. 1.5-diazabicyclo[4.3.0] nonane-5-ene, 1,8-diazabicyclo[5,4,0]undecane-7-ene, N-methylmorpholine, and 4-dimethylaminopyridine. Desirably, the reaction is conducted in an inert solvent, e.g. tetrahydrofuran, dioxane, n-hexane, or toluene under cooling with ice or at room temperature though feasible under heating.

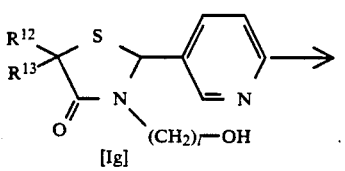

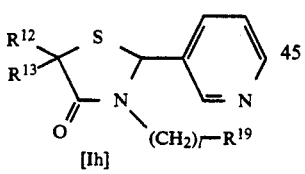

In this equation, $R^{19}$ denotes halogen and $R^{12}$, $R^{13}$, and l are as defined above.

That is, the compound [Ih] can be prepared by replacing the hydroxy group of compound [Ig] with a halogen atom. This replacement can be achieved by using, for example, phosphorus tribromide, phosphorus pentachloride, or thionyl chloride as a halogenating reagent, preferably in the presence of an organic base such as pyridine. Thus, the compound [Ih] is obtained by carrying out the reaction in a solvent selected from halogenated hydrocarbons such as dichloromethane, chloroform, and 1,2-dichloroethane and aromatic hydrocarbons such as benzene and toluene while cooling with ice or heating under reflux. The use of a triphenyl or phosphine-carbon tetrachloride mixture is an effective methods of the halogenation.

In this equation, $R^{20}$ denotes $C_1$–$C_4$ alkyl or $C_1$–$C_4$ alkanoyl, X denotes leaving group, and $R^{12}$, $R^{13}$ and l are as defined above.

That is, the compound [Ii] can be prepared by reacting the compound [Ig] with the compound [VIII], preferably in the presence of a base. When $R^{20}$ is $C_1$–$C_4$ alkyl, the reaction is carried out in a solvent such as dimethylformamide, dimethylsulfoxide, or tetrahydrofuran in the presence of an inorganic base such as sodium hydride, potassium hydroxide, or potassium carbonate or an organic base such as pyridine or triethylamine while cooling with ice or heating under reflux. When $R^{20}$ is $C_1$–$C_4$ alkanoyl, the reaction is conducted desirably by using an organic base such as pyridine or triethylamine and a solvent selected from aromatic hydrocarbons such as benzene and toluene, ether solvents such as tetrahydrofuran, the above-mentioned organic bases, and alkanoylating reagents, while cooling with ice or heating under reflux.

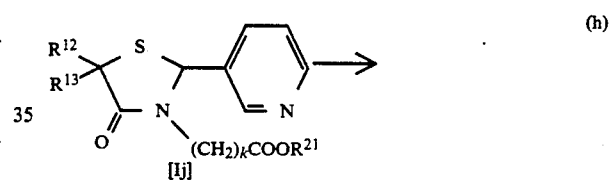

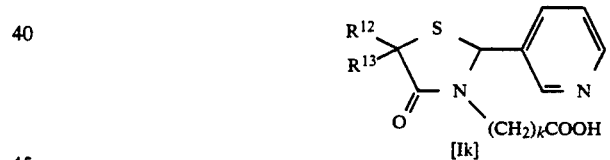

In this equation, $R^{21}$ denotes $C_1$–$C_4$ alkyl and $R^{12}$, $R^{13}$ and k are as defined above.

The compound [Ik] can be prepared by hydrolyzing the compound [Ij] in the presence of an acid or base catalyst under conditions of common ester hydroalysis (S. Coffey, "Rodd's Chemistry of Carbon Compounds" 2ed Ed., Vol. 1c DLsevier (1955), p.92). For instance, the reaction is conducted at room temperature or under heating in the presence of sodium hydroxide or potassium hydroxide by using an alcohol such as methanol or ethanol or water as a solvent.

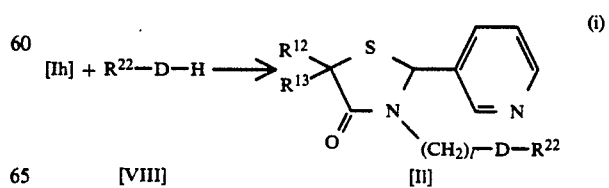

In this equation, $R^{22}$ denotes $C_1$–$C_4$ alkyl or $C_1$–$C_4$ alkanoyl and $R^{12}$, $R^{13}$, D, and l are as defined above.

The compound [II] is prepared by reacting the compound [Ih] with the compound [VIII], preferably in the presence of a base. For instance, the reaction is conducted in a solvent selected from aromatic hydrocarbons such as benzene and toluene, halogenated hydrocarbons such as chloroform and dichloroethane, ethers such as tetrahydrofuran, and dimethylformamide and the like in the presence of an inorganic base such as sodium hydroxide, potassium hydroxide, potassium carbonate, or sodium hydrogencarbonate or an organic base such as pyridine or triethyl amine, while cooling with ice or heating under reflux.

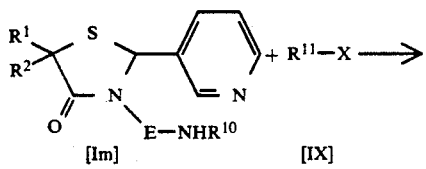

(j)

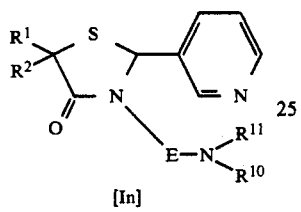

[In]

In this equation, X, $R^1$, $R^2$, $R^{11}$, $R^{10}$, and E are as defined above.

The compound [In] can be prepared by reacting the compound [Im] with the compound [IX] in the presence of a base. Suitable bases include; organic alkali metal compounds, e.g. butyllithium; alkali metal amides, e.g. lithium diisopropylamide; and alkali metal hydrides, e.g. sodium hydride. The reaction is conducted in a common organic solvent (e.g. tetrahydrofuran, dioxane, n-hexane, toluene, or dimethylformamide) fitted for the base to use, preferably under cooling with ice or at room temperature though the reaction is feasible under heating.

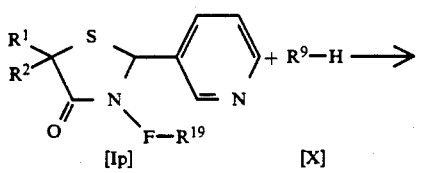

(k)

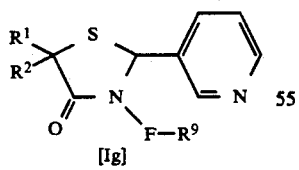

[Ig]

In this equation, $R^1$, $R^2$, $R^9$, $R^{19}$, and F are as defined above.

The compound [Ig] can be prepared by reacting the compound [Ip] with the compound [X] in the presence of a base. Suitable bases include; organic alkali metal compounds, e.g. butyllithium; alkali metal amides, e.g. lithium diisopropylamide; and alkali metal hydrides, e.g. sodium hydride. The reaction is conducted in a common organic solvent (e.g. tetrahydrofuran, dioxane, n-hexane, toluene, or dimethylformamide) fitted for the base to use, preferably under cooling with ice or at room temperature though the reaction is feasible under heating.

Those raw materials for use in the above reactions are known compounds per se or can be synthesized by known methods. For example, the compounds [II], [III], and [XVII] could be prepared, as shown later in reference examples, in the following ways:

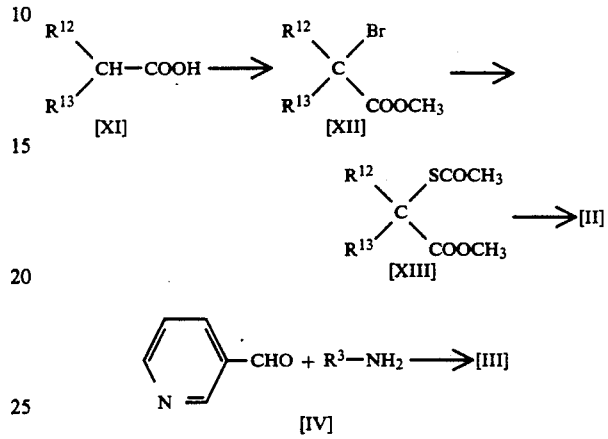

In these equations, $R^{12}$, $R^{13}$ and $R^3$ are as defined above.

That is, the starting compound [XI] was esterified and brominated according to the method of E. Schwenk et al. (J. Am. Chem. Soc., 70, 3626 (1948)) to give a compound [XII], which was then converted into a thiol ester derivative [XIII] according to the method described in Shin Jikken Kagaku Koza (A New Course of Experimental Chemistry), Vol. 14, p. 1712. The compound [XIII] was hydrolyzed with a base such as sodium hydroxide or potassium hydroxide in a water-alcohol solvent mixture, thereby preparing the mercaptan derivative [II].

The Schiff's base compound [III] was prepared by subjecting 3-pyridinecarboxyaldehyde and a primary amine [IV] to dehydration-condensation according to the method described in Shin Jikken Kagaku Koza, Vol. 14, page 1410.

The compound [XVII] was prepared by the following route.

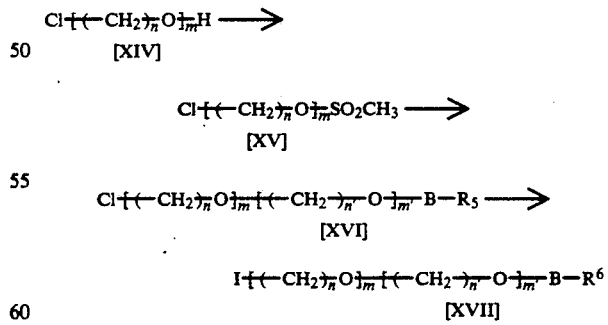

That is, a starting compound [XIV] was converted into a methanesulfonyl derivative [XV] according to the method described in Shin Jikken Kagaku Koza, Vol. 14(III), page 1797. This compound [XV] was converted into a compound [XVI] according to the method of W. T. Olson et al (J. Am. Chem. Soc., 69, 2451 (1947)). Then, the compound [XVII] was derived from the compound [XVI] according to the method described in Shin Jikken Kagaku Koza, Vol. 14(I), page 438.

Starting compounds [Ia], [Ic], [Ie], [Ig], [Ih], [Ij], [Im], and [Ip], which are also objective compounds of the present invention, were prepared, for example, according to the above process (a).

When used as medicines, the present inventive compounds represented by the general formula [I] given above and their acid addition salts can be administered orally or parenterally. That is, they can be administered orally in usual dosage forms such as tablets, capsules, sirups, suspensions, and solutions or parenterally in the form of injectable liquids such as solutions, emulsions, and suspensions. Further, they can be administered rectally in suppository form and also administered in the form of inhalation sprays as well as in the form of percutaneous agents.

The above-mentioned suitable dosage forms can be prepared by compounding the present active compounds with conventional acceptable carriers, excipients, binders, stabilizers, etc. For use in the form of injections, it is possible to add acceptable buffers, solubilizing aids, isotonic agents, etc. to the present active compounds.

While the dose and the frequency of dosage depend upon the condition, age, and weight of the patient, the dosage form, etc., about 1 to 5000 mg, preferably 10 to 300 mg, of the present active compound is generally administered once or in parts a day for an adult.

ACTION OR EFFECT OF THE INVENTION

It has been revealed that the present inventive compound [I] has pharmacological effects desirable as a curative agent for PAF-induced diseases. That is, the compound [I] exhibits a powerful and selective PAF-antagonism and is excellent in effects also in vivo. The pharmacological effect of the present inventive compound is described below in detail.

TEST IN VITRO FOR INHIBITION OF PLATELET AGGREGATION (A) Inhibition of Rabbit Platelet Aggregation The inhibition of PAF-induced platelet aggregation was examined by using a platelet-rich plasma (PRP) of rabbit according to the method of Mustard et al. [J. F. Mustard et al., J. Lab. Clin. Med., 64, 548 (1964)], which is an improvement of the method of Born [G. V. R. Born, J. Physiol., London, 162, 67 (1962)]. That is, 80–100 ml of blood per animal was collected from carotid arteries of male rabbits of the Japanese white breed without anesthesia into a polyethylene vessel containing 1/10 the volume of a 3.8% sodium citrate solution. A portion (about 3 ml) of the collected blood was centrifuged at a high speed (11,000 rpm) for 60 seconds, giving a platelet-poor plasma (PPP) as supernatant. The remainder of the blood was centrifuged at low speed (1000 rpm) for 10 minutes, giving a platelet-rich plasma (PRP) as supernatant.

The degree of platelet aggregation was determined by nephelometry with an aggregometer (Hematracer, Niko Bioscience Co.) while stirring the PRP at 1000 rpm at 37° C. The platelet aggregation activity was expressed in terms of the light transmittance (%), the value of PRP being taken as 0% and the value of PPP as 100%. A portion (0.2 ml) of the PRP was placed in a glass cuvette containing a silicone-treated stirring iron rod, and 2 μl of dimethylsulfoxide was added. After 2 minutes, PAF dissolved in 0.25% BSA physiological saline was added to give a final PAF concentration of 0.005 μl/ml, and the maximum aggregation was determined. To examine the inhibitory activity of test compounds on the platelet aggregation caused by PAF, 2 μl of a dimethylsulfoxide solution of each test compound was added in place of the dimethylsulfoxide. The percentage inhibition by the test compound of PAF-induced platelet aggregation was calculated according to the following equation and the value of $IC_{50}$ was determined.

Percentage inhibition $$\text{Percentage inhibition} = \left[1 - \frac{\text{Max. aggregation after addition of test compound}}{\text{Max. aggregation after addition of dimethylsulfoxide}}\right] \times 100$$

Results of the test are shown in Table 1.

TABLE 1

| Inhibition of PAF-induced rabbit platelet aggregation | |
|---|---|
| Test compound (compound No.) | $IC_{50}$ value [μg/ml] |
| 2 | 4.0 |
| 3 | 3.5 |
| 7 | 2.0 |
| 8 | 3.6 |
| 9 | 1.6 |
| 15 | 2.6 |
| 18 | 3.0 |
| 24 | 2.0 |
| 25 | 10 |
| 27 | 0.02 |
| 28 | 0.20 |
| 30 | 4.2 |
| 37 | 0.7 |
| 42 | 2.5 |
| 43 | 1.2 |
| 46 | 1.9 |
| 47 | 1.4 |
| 49 | 2.4 |
| 50 | 4.6 |
| 51 | 1.4 |
| 67 | 0.45 |
| 69 | 0.24 |
| 71 | 0.32 |
| 73 | 0.07 |
| 75 | 0.06 |
| 76 | 0.20 |
| 77 | 0.034 |
| 78 | 0.14 |
| 79 | 0.05 |
| 80 | 0.35 |
| 81 | 0.10 |
| 82 | 0.60 |
| 83 | 0.27 |
| 108 | 0.70 |
| 127 | 1.7 |
| 128 | 4.2 |
| 130 | 4.2 |
| 131 | 0.14 |
| 133 | 0.18 |
| 135 | 0.15 |
| 137 | 0.19 |
| 150 | 0.16 |
| 154 | 2.4 |
| 165 | 0.30 |
| 169 | 0.026 |
| 170 | 0.052 |
| 171 | 4.2 |
| 172 | 0.30 |
| 178 | 1.5 |
| 181 | 5.0 |

(B) Inhibition of Human Platelet Aggregation

The inhibition of PAF-induced platelet aggregation was tested by using human PRP. The test was conducted according to the procedure of the above case of rabbit, thereby evaluating the percentages inhibition and $IC_{50}$ values of test compounds at final PAF concentrations of 0.3 $\mu$M and 1 $\mu$M. Results of the evaluation are shown in Table 2.

TABLE 2

| | Inhibition of PAF-induced human platelet aggregation | |
|---|---|---|
| Test compound | $IC_{50}$ value ($\mu$g/ml) PAF concentration | |
| (Compound No.) | 0.3 $\mu$M | 1 $\mu$M |
| 2 | 5.5 | — |
| 3 | 6.0 | — |
| 27 | 0.2 | 0.4 |
| 28 | 1.2 | 2.5 |
| 33 | 5.5 | — |
| 108 | 1.8 | 6.0 |

None of the test compounds at a concentration of 10 $\mu$g/ml affected at all the aggregation induced by other aggregating agents, e.g. ADP and collagen.

Test in Vivo for Inhibition of PAF-Induced Blood Concentration

Guinea pigs under anesthesia with urethane (6.25 mg/kg injected into the abdominal cavities) were cannulated through cartoid arteries and jugular veins. The carotid artery cannulae were used for blood sampling and the jugular vein cannulae for the intravenous injection of test compound and PAF.

Compound No. 27 was suspended in 10% Nikkol® liquid to a concentration of 3 mg/ml, and 1 ml/kg of the resulting suspension was administered through the jugular vein cannulae. Two minutes later, 1 ml/kg of a 0.1 $\mu$g/ml PAF solution was administered through the jugular vein cannulae. Then, blood was sampled at times. The blood samples were each centrifuged at 11,000 rpm for 5 minutes and the hematocrit values were measured to determine the maximum increase (blood concentration) in hematocrit value.

For a control, 0.5% methyl cellulose solution was administered in place of compound No. 27.

The percentage inhibition of the PAF-induced blood concentration by compound No. 27 was calculated according to the following equation:

$$\text{Percentage inhibition} = \left[1 - \frac{\text{PAF-induced average maximum increase hematocrit value in animals injected with compound 27}}{\text{PAF-induced average maximum increase in hematocrit value in control animals}}\right] \times 100$$

The found percentage inhibition was 87%.

Results of the same test on other compounds are shown in Table 3.

TABLE 3

| Inhibiton of PAF-induced blood concentration | | |
|---|---|---|
| Test compound (Example No.) | Dose 3 mg/kg.iv | Dose 30 mg/kg.iv |
| 2 | 53% | — |
| 3 | — | 58% |

TABLE 3-continued

| Inhibiton of PAF-induced blood concentration | | |
|---|---|---|
| Test compound (Example No.) | Dose 3 mg/kg.iv | Dose 30 mg/kg.iv |
| 28 | — | 92% |

Test for Inhibition of Fatal Effect of PAF on Mice

Male ICR mice (perchased Charles River Co.) aged 4 weeks were anesthetized by injecting subcutaneously 100 mg/kg of Isomital® soda (sodium amobarbital supplied by Nippon Shinyaku Co., Ltd.). After 18 minutes, the mice were injected with a test compound or a solvent through tail veins. The test compound was dissolved in a 0.2M phosphate buffer solution to a concentration of 1 mg/ml and 10 ml/kg of this solution was injected (dose of test compound: 10 mg/kg). Two minutes after this administration, the mice were injected with 10 $\mu$g/kg of PAF through tail veins. The PAF was dissolved in physiological saline containing 0.25% of bovine serum albumin to a concentration of 2 $\mu$g/ml, and the mice were injected with 5 ml/kg of this solution.

After PAF administration, the mice were observed and the survival rate of mice 2 hours later was determined. The found survival rates were as follows:

| Test Compound No. | Survival rate (%) |
|---|---|
| Control | 0 |
| 174 | 80 |
| 175 | 60 |
| 182 | 100 |

The results of the above tests indicate that the antagonistic action of the present inventive compound [I] on PAF is powerful and highly specific. This action was confirmed by not only in vitro tests but also in vivo tests. Accordingly, the present inventive compound [I] is very useful as a preventive and curative agent for PAF-induced diseases, for example, various kinds of inflammation, circulatory diseases, allergic diseases, and gastrointestinal ulcers.

The present invention is illustrated with reference to the following examples and reference examples, which are not intended to restrict the scope of the invention.

REFERENCE EXAMPLE 1

Preparation of 2-mercaptoundecanoic acid (I) Methyl 2-bromoundecanoate

Undecanoic acid (100 g, 0.54 mol) was added to thionyl chloride (108 ml, 1.48 mol) and this mixture was refluxed for 2 hours. Then, bromine (29 ml, 0.57 mol) was added dropwise over 1.5 hours under reflux. Reflux was continued for 5 additional hours.

The resulting mixture was cooled to room temperature, methanol (250 ml, 6.1 mol) was added dropwise over 30 minutes, and this reaction mixture was left standing overnight. After addition of aqueous NaCl, the product mixture was extracted twice with ether. The extract was washed with aqueous $NaHCO_3$, aqueous $Na_2SO_3$, and aqueous NaCl, and then dried. The solvent was removed in vacuo, giving crude methyl 2- bromoundecanoate (145 g, 97% yield). IR (neat) [cm$^{-1}$]; 2920, 2850, 1736, 1432, 1144

(II) Methyl 2-acetylthioundecanoate

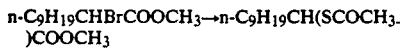

Dry dimethylformamide (600 ml) was added to 60% sodium hydride (22.5 g, 0.56 mol) under a stream of nitrogen. The mixture was cooled to 0° C., thioacetic acid (51.6 g, 0.68 mol) was added dropwise at 0° to 10° C., and the mixture was kept between those temperatures for 1 hour. Then crude methyl 2-bromoundecanoate (145 g, 0.52 mol) from above (I) was added dropwise at 0° to 10° C., and the mixture was kept between those temperatures for 2 hours. After addition of aqueous NaCl, the product mixture was extracted twice with ether. The extract was washed with aqueous NaHCO$_3$, aqueous Na$_2$SO$_3$, and aqueous NaCl, and dried. The solvent was removed in vacuo and the residue was purified by column chromatography, giving methyl 2-acetylthioundecanoate (108 g, 76% yield). IR (neat) [cm$^{-1}$]; 2920, 2860, 1738, 1698, 1435, 1350 1152, 950.

(III) 2-Mercaptoundecanonic acid

Methyl 2-acetylthioundecanoate (122.2 g, 0.44 mol) from above (II) was dissolved in methanol (527 ml). Water (226 ml) and NaOH (67 8 g, 1.67 mol) were added in turn. The mixture was heated under reflux for 2 hours and then cooled. After addition of water, the product mixture was extracted twice with hexane. The aqueous layer was acidified to a pH of 1 to 2 with conc. HCl, and extracted twice with ether. The combined extracts were washed with aqueous NaCl, and dried. The solvents were removed in vacuo, giving 2-mercaptoundecanoic acid (95.54 g, 98% yield). IR (CHCl$_3$) [cm$^{-1}$]; 2850, 1705.

REFERENCE EXAMPLE 2

Preparation of N-nicotinylidenemethylamine

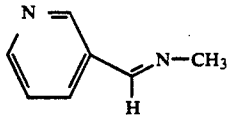

Nicotinaldehyde (10.7 g, 0.1 mol) was dissolved in toluene (100 ml). A 40% aqueous methylamine (23.3 g, 0.3 mol) solution was added. This mixture was subjected to azeotropic dehydration for 3 hours. The produce mixture was concentrated under reduced pressure, giving N-nicotinylidenemethylamine (11.7 g, 98% yield). NMR (CDCl$_3$ δ) [ppm]; 3.53 (3 H, d, J=1.7 Hz), 7.3–8.85 (5 H, m).

REFERENCE EXAMPLE 3

Preparation of 1-iodo-2-[2-(1-methylethoxy)ethoxy]-ethane (I) 1-Chloro-2-(2-methanesulfoxy)ethane 2-(2-Chloroethoxy)ethanol (20 g, 0.16 mol) was dissolved in dichloromethane (200 ml), and triethylamine (16.2 g, 0.16 mol) was added. This reaction mixture was cooled with ice and methanesulfonyl chloride (18.3 g, 0.16 mol) was added dropwise over 1 hour. Then the mixture was further stirred for 1 hour while continueing ice-cooling. Saturated aqueous NaHCO$_3$ (40 ml) was added dropwise to the product mixture under cooling with ice, and the separated aqueous layer was extracted with dichloroethane. The extract was washed with 10% aqueous HCl, saturated aqueous NaCl, saturated aqueous NaHCO$_3$, and saturated aqueous NaCl in that order, and dried over MgSO$_4$. Then the solvent was removed in vacuo, giving 1-chloro-2-(2-methanesulfoxyethoxy)ethane (33.6 g, 100% yield). IR (CHCl$_3$) [cm$^{-1}$]; 1355, 1300, 1170, 1135, 1115, 969, 913. NMR (CDCl$_3$) [δ ppm]; 4.41–4.38 (2 H, m), 3.81–3.76 (4 H, m), 3.65 (2 H, t, J=5.9 Hz), 3.08 (3 H, S).

(II) 1-Chloro-2-[2-(1-methylethoxy)ethoxy]ethane

Dry isopropyl alcohol (12.2 ml, 160 mol) was placed in a dried 4-necked flask and finely-cut pieces of metallic sodium (920 mg, 40 mmol) was added under a stream of nitrogen. The mixture was heated under reflux for 3 hours. Then, heating was stopped and 1-chloro-2-(2-methanesulfoxyethoxy)ethane (8.4 g) was added all at once. After heat generation had ceased, the product mixture was cooled to room temperature, dil. aqueous HCl was added, and the mixture was extracted twice with ether. The extract was washed with saturated aqueous NaHCO$_3$ and saturated aqueous NaCl, and dried over MgSO$_4$. Then the solvent was removed in vacuo and the residue was distilled under reduced pressure, giving 1-chloro-2-[2-(1-methylethoxy)ethoxy]ethane (3.7 g, 55% yield) at 114° to 121° C. under 73 to 83 mmHg. IR (CHCl$_3$) [cm$^{-1}$]; 2870, 1460, 1382, 1370, 1335, 1300, 1120, 1090, 970, 912. NMR (CDCl$_3$) [δ ppm]; 3.7 (2 H, t, J=5.9 Hz), 3.68–3.57 (7 H, m), 1.17 (6 H, d, J=5.9 Hz).

(III) 1-Iodo-2-[2-(1-methylethoxy)ethoxy]ethane

1-Chloro-2-[2-(1-methylethoxy)ethoxy]ethane (1.0 g, 6.0 mmol) was dissolved in acetone (10 ml), and sodium iodide (1.2 g, 8.0 mmol) was added. The mixture was refluxed for 2 hours and then cooled to room temperature. The reaction mixture was filtered to remove the formed NaCl and the filtrate was evaporated in vacuo. Water was added to the residue and the mixture was extracted twice with ether. The extract was washed with 5% aqueous Na$_2$SO$_3$ and saturated aqueous NaCl, and dried over MgSO$_4$. Then the solvent was removed in vacuo under 20° C. and the residue was purified by column chromatography (Si60 ®, hexane-ethyl acetate=20:1), giving 1-iodo-[2-(2-methylethoxy)ethoxy]ethane (1.0 g, 66% yield). IR (CHCl$_3$) [cm$^{-1}$]; 2870, 1465, 1885, 1374, 1340, 1120, 1090, 970. NMR (CDCl$_3$) [δ ppm]; 3.77 (2 H, t, J=6.9 Hz), 3.66–3.57 (6 H, m), 3.26 (1 H, t, J=6.9 Hz) 1.17 (6 H, d, J=6.2 Hz).

REFERENCE EXAMPLE 4

Preparation of 1-chloro-2-(2-t-butyldimethylsilyloxyethoxy)ethane

Imidazole (17.8 g, 261 mmol) was dissolved in dimethylformamide (100 ml) and t-butyldimethylsilyl chloride (36.3 g, 241 mmol) was added and stirred. 2-(2-chloroethoxy)ethanol (25.0 g, 200 mmol) was added dropwise over 1 hour under cooling with ice, and the mixture was stirred for 1 further hour, left standing overnight at room temperature, and then poured into saturated aqueous NaCl (500 ml). The resulting mixture was extracted twice with ether. The extract was washed twice with saturated aqueous NaCl, and dried over MgSO$_4$. Then the solvent was removed in vacuo, giving 1-chloro-2-(2-t-butyldimethylsilyloxyethoxy)ethane (47.8 g, 100% yield). IR (CHCl$_3$) [cm$^{-1}$]; 2920, 2850, 1460, 1100, 930. NMR (CDCl$_3$) [δ ppm]; 3.94–3.90 (4 H, m) 3.79–3.72 (4 H, m), 1.05 (9 H, s), 0.22 (6 H, s).

EXAMPLE 1

Preparation of 3,5-dimethyl-2-(3-pyridyl)thiazolidin-4-one (compound No. 1)

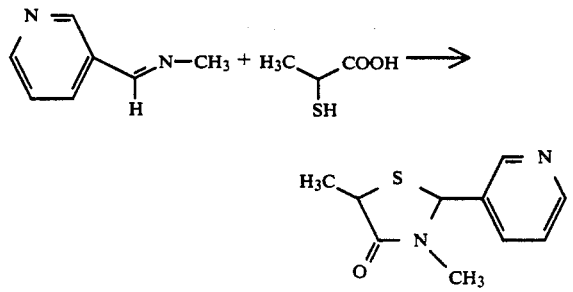

N-Nicotinylidenemethylamine (12.0 g, 0.1 mmol) was dissolved in toluene (100 ml) and thiolactic acid (10.6 g, 0.1 mol) was added. The mixture was subjected to azeotropic dehydration for 3 hours. The product mixture was cooled and washed with 5% aqueous NaHCO$_3$ solution, and dried. The solvent was removed in vacuo. The residue was subjected to recrystallization from ether, giving 3,5-dimethyl-2-(3-pyridyl)thiazolidin-4-one (15.6 g, 75% yield). m.p. 89.5°–92° C. IR (nujol) [cm$^{-1}$]; 1670, 1582, 1017, 719.

EXAMPLE 2

3,5-Dimethyl-2-(3-pyridyl)thiazolidin-4-one (5 g) from Example 1 was subjected twice to recrystallization from a 1:1 ethyl acetate-hexane mixture, giving its cis-isomer (compound No. 2). The filtrate was subjected to medium-pressure liquid chromatography (hexane-ethanol) to isolate the trans-isomer (compound No. 3). cis-Isomer (compound No. 2) m.p. 98.5°–99° C. trans-Isomer (compound No. 3) m.p. 81°–82° C.

EXAMPLE 3

Preparation of 3,5-dimethyl-2-(3-pyridyl)thiazolidin-4-one (compound No. 1) (another method)

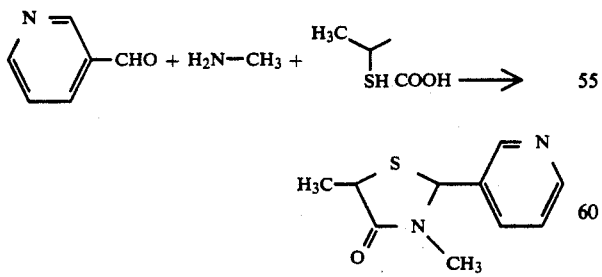

Nicotinaldehyde (10.7 g, 0.1 mol) was dissolved in toluene (100 ml), and a 40% aqueous methylamine (23.3 g, 0.3 mol) solution and thiolactic acid (10.6 g, 0.1 mol) were added. The mixture was subjected to azeotropic dehydration for 3 hours. The product mixture was cooled, washed with 5% aqueous NaHCO$_3$, and dried. The solvent was removed in vacuo, and the residue was subjected to recrystallization from ether, giving 3,5-dimethyl-2-(3-pyridyl)thiazolidin-4-one (14.2 g, 68% yield). m.p. 90°–92° C.

EXAMPLE 4

Preparation of 3-methyl-2-(3-pyridyl)thiazolidin-4-one (compound No. 4)

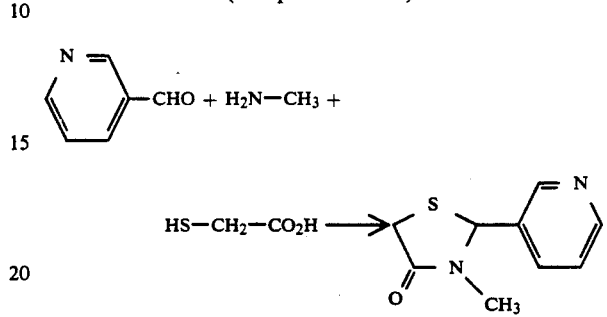

According to the procedure of Example 3, the title compound was prepared by using nicotinaldehyde, a 40% aqueous methylamine solution, and thioglycolic acid as charge stock. m.p. 96.5°–97.5° C. IR (nujol) [cm$^{-1}$]; 1670, 1583, 1236, 1109, 1005, 717.

EXAMPLE 5

Preparation of 5-methyl-2-(3-pyridyl)thiazolidin-4-one (compound No. 5)

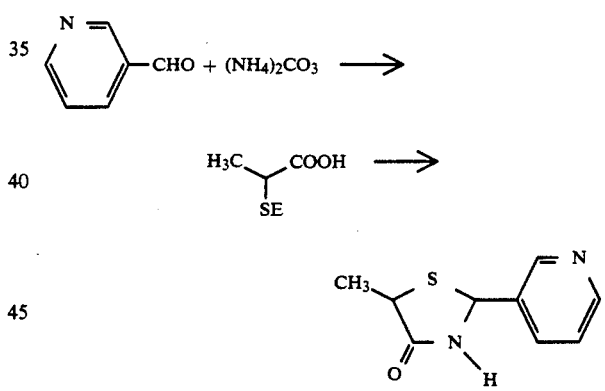

According to the procedure of Example 3, the title compound was prepared by using nicotinaldehyde, ammonium carbonate, and thiolactic acid as charge stock. m.p. 109.5°–110.5° C. IR (nujol) [cm$^{-1}$]; 1680.

EXAMPLE 6

Preparation of 3-(2-hydroxyethyl)-5-methyl-2-(3-pyridyl)thiazolidin-4-one (compound No. 6)

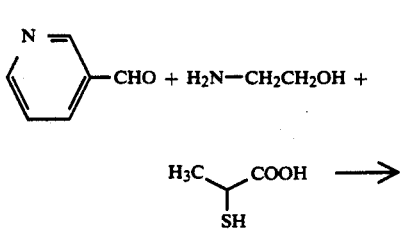

-continued

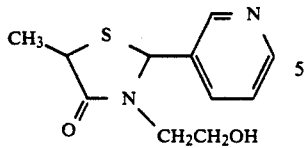

According to the procedure of Example 3, the title compound was prepared by using nicotinaldehyde, ethanolamine, and thiolactic acid as charge stock. NMR (δ, CDCl₃) [ppm]; 1.63 (1 H, d, J=6,8 Hz), 1.66 (2 H, d, J=6.8 Hz), 2.8-4.2 (6 H, m), 5.83 (1 H, s). IR (CDCl₃) [cm⁻¹]; 3400, 2940, 1670, 1593, 1580, 1450, 1360, 1070.

EXAMPLE 7

Preparation of 5-butyl-3-methyl-2-(3-pyridyl)-thiazolidin-4-one (compound No. 7)

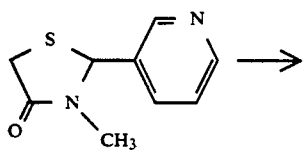

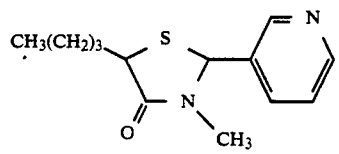

Dry diisopropylamine (1 ml, 5.7 mmol) was added to dry tetrahydrofuran (3 ml), and a butyllithiium solution (3.9 ml, 6.2 mmol) in hexane was added dropwise at −40° C., the mixture was kept at −10° C. for 1 hour. A solution of 3-methyl-2-(3-pyridyl)thiazolidin-4-one (1 g, 5.2 mmol) in dry tetrahydrofuran (7 ml) was added dropwise to the mixture at −20° to −10° C. After this reaction mixture had been kept between those temperatures for 1 hour, there were added at −10° C. 1-bromobutane (0.78 g, 5.7 mmol) dissolved in tetrahydrofuran (2 ml), sodium iodide (0.77 g, 5.2 mmol), and hexamethylphosphorotriamide (1 ml). This reaction mixture was kept at room temperature for 2 hours. The resulting mixture, after addition of a phosphate buffer (pH 7.0), was extracted with ethyl acetate. The extract was dried over anhydrous Na₂SO₄ and filtered. The filtrate was concentrated by evaporation under reduced pressure. The residue was chromatographed on silica gel (hexeneethyl acetate), giving 5-butyl-3-methyl-2-(3-pyridyl)-thiazolidin-4-one (250 mg, 20% yield). NMR (CDCl₃) δ [ppm]; 0.93 (3 H, t, J=7.0 Hz), 1.2–2.3 (6 H, m), 2.74 (3 H, m), 3.9–4.3 (1 H, m), 5.4–5.5 (1 H, m). IR (CHCl₃) [cm⁻¹]; 2925, 2855, 1670, 1590, 1578, 1390, 1303, 1020.

EXAMPLE 8

Preparation of 5,5,3-trimethyl-2-(3-pyridyl)-thiazolidin-4-one (compound No. 8)

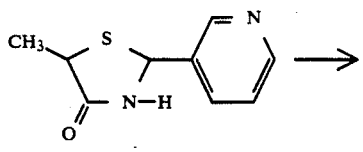

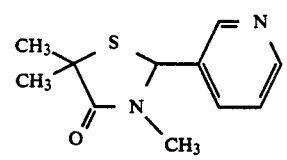

Dry diisopropylamine (0.95 ml, 5.3 mmol) was added to dry tetrahydrofuran (3 ml). Further a butyllithium solution (3.6 ml, 5.8 mmol) in hexane was added dropwise at −40° C. The mixture was kept at −10° C. for 1 hour. Then a solution of 3,5-dimethyl-2-(3-pyridyl)-thiazolidin-4-one (1 g, 4.8 mmol) in dry tetrahydrofuran (7 ml) was added dropwise at −20° to −10° C. After this reaction mixture had been kept between those temperatures for 1 hour, methyl iodide (0.75 g, 5.3 mmol) dissolved in dry tetrahydrofuran (2 ml) was added at −20° to −10° C. This reaction mixture was heated for 2 hours up to 0° C. and then kept at the same temperature for 2 hours. The resulting mixture, after addition of a phosphate buffer (pH 7.0), was extracted with ethyl acetate. The extract was dried over anhydrous Na₂SO₄ and filtered. The filtrate was concentrated under reduced pressure, and subjected to medium-pressure liquid chromatography (hexane-acetone) and then to recrystallization from a 1:1 ether-hexane mixture, giving 5,5,3-trimethyl-2-(3-pyridyl)thiazolidin-4-one (0.42 g, 39% yield). NMR (CDCl₃) δ [ppm]; 1.62 (3 H, s), 1.68 (3 H, s), 2.74 (3 H, s), 5.51 (1 H, s). IR (nujol) [cm⁻¹]; 1668, 1590, 1390, 1310, 1135, 1071, 1021.

EXAMPLE 9

Preparation of 5,5-di(cyclohexylmethyl)-3-methyl-2-(3-pyridyl)-thiazolidin-4-one (compound No. 184)

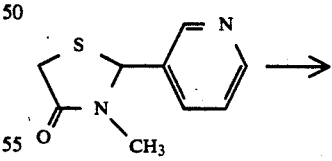

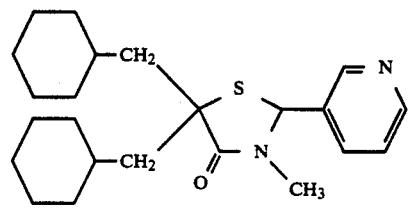

Dry diisopropylamine (2.76 ml, 15.8 mmol) was added to dry tetrahydrofuran (9 ml). Further a n-butyllithium solution (10.6 ml, 16.2 mmol) in hexane was added dropwise at −20° to −30° C. The mixture was kept between those temperatures for 1 hour. Then a solution of 3-methyl-2-(3-pyridyl)thiazolidin-4-one (3 g, 15.4 mmol) in dry tetrahydrofuran was added dropwise at −78° C. After this reaction mixture had been kept at the same temperature for 1 hour, bromomethylcyclohexane (3.01 g, 17.0 mmol) and sodium iodide (2.31 g, 15.4 mmol) were added at −78° C. This reaction mixture was heated up to room temperature and kept standing overnight. The resulting mixture, after addition of aqueous NaCl, was extracted with ethyl acetate. The extract was washed with aqueous NaCl, dried, and the solvent was removed in vitro. The residue was chromatographed on silica gel, giving 5,5-di(cyclohexylmethyl)-3-methyl-2-(3-pyridyl)thiazolidin-4-one (250 mg, 4.2% yield). IR (CHCl$_3$) [cm$^{-1}$]; 2920, 1675, 1640, 1390.

EXAMPLE 10

Preparation of 3-ethoxycarbonylmethyl-5-methyl-2-(3-pyridyl)-thiazolidin-4-one (compound Nos. 9, 10)

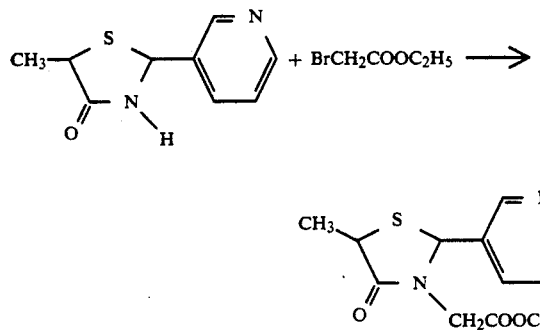

5-Methyl-2-(3-pyridyl)thiazolidin-4-one (10 g, 51.5 mmol) and ethyl bromoacetate (6.85 ml, 61.8 mmol) were dissolved in dry dimethylformamide (50 ml), and 60% sodium hydride (2.16 g, 54.1 mmol) was added in limited amounts to the solution at 0° to 10° C. This reaction mixture was kept between those temperatures for 1 hour. The mixture, after addition of aqueous NaCl, was extracted with ethyl acetate. The extract was washed with aqueous NaCl, dried, and the solvent was removed in vacuo. The residue was chromatographed on silica gel, giving the cis-isomer (5.8 g) (compound No. 9) and the trans-isomer (2.1 g) (compound No. 10) of the title compound (55% yield). Compound No. 9: cis-isomer NMR (CDCl$_3$, δ) [ppm]; 1.24 (3 H, t, J=7.2 Hz), 1.67 (3 H, d, J=7.1 Hz), 5.81 (1 H, s). IR (CHCl$_3$) [cm$^{-1}$]; 2950, 1740, 1683, 1587, 1575, 1441, 1370, 1014. Compound No. 10: trans-isomer NMR (CDCl$_3$, δ) [ppm]; 1.25 (3 H, t, J=7.2 Hz), 1.68 (3 H, d, J=7.1 Hz), 5.83 (1 H, d, J=1.7 Hz). IR (CHCl$_3$) [cm$^{-1}$]; 2950, 1739, 1685, 1585, 1572, 1370, 1345, 1012.

EXAMPLE 11

Preparation of 3-(2-chloroethyl)-5-methyl-2-(3-pyridyl)thiazolidin-4-one (compound Nos. 11, 12)

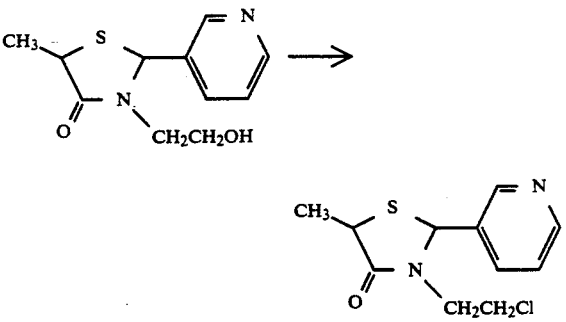

3-(2-Hydroxyethyl)-5-methyl-2-(3-pyridyl)-thiazolidin-4-one (18.75 g, 78.7 mmol) was dissolved in methylene chloride (200 ml). Pyridine (9.55 ml, 118 mmol) was added and further, thionyl chloride (20 ml, 274 mmol) was added dropwise over 2 hours at 0° to 5° C. This reaction mixture was kept between those temperatures for 5 hours. The resulting mixture was washed with aqueous NaHCO$_3$ and aqueous NaCl, dried, and the solvent was removed in vacuo. The residue was chromatographed on silica gel and upon recrystallization from hexane-ether, gave 2,5-cis-3-(2-chloroethyl)-5-methyl-2-(3-pyridyl)thiazolidin-4-one (7.11 g) and 2,5-trans-3-(2-chloroethyl)-5-methyl-2-(3-pyridyl)-thiazolidin-4-one (3.11 g), (51% yield). Compound No. 12: cis-isomer, m.p. 76°-77° C. Compound No. 11: trans-isomer, m.p. 112.5°-113.5° C.

EXAMPLE 12

Preparation of 3-(2-methoxyethyl)-5-methyl-2-(3-pyridyl)thiazolidin-4-one (compound No. 13)

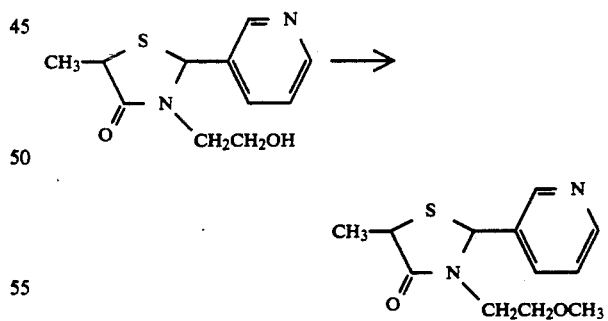

Methyl iodide (0.72 g, 5.0 mmol) was added to a solution of 3-(2-hydroxyethyl)-5-methyl-2-(3-pyridyl)-thiazolidin-4-one (1 g, 4.2 mmol) in dry dimethylformamide (5 ml), and 40% sodium hydride (176 mg, 4.4 mmol) was added in limited amounts of the mixture under cooling with ice. Then, cooling with ice was continued for 1 hour. The product mixture was poured into aqueous NaCl, and extracted with ethyl acetate. The extract was washed with water, dried over anhydrous Na$_2$SO$_4$, and filtered. The filtrate was concentrated and subjected to medium-pressure chromatography (hexane-acetone), giving 3-(2-methoxyethyl)-5-methyl-2-(3-pyridyl)-thiazolidin-4-one (0.51 g, 48% yield). NMR (CDCl₃) δ [ppm]; 1.62 (0.75 H, d, J=7.1 Hz), 1.66 (2.5 H, d, J=7.1 Hz), 3.28 (2.25 H, s), 3.3 (0.75 H, s), 5.85 (1 H, s) IR (CHCl₃) [cm⁻¹]; 2935, 1670, 1589, 1576, 1445, 1408, 1300, 1113.

EXAMPLE 13

Preparation of 3-(2-acetoxyethyl)-5-methyl-2-(3-pyridyl)thiazolidin-4-one (compound No. 14)

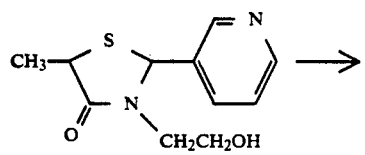

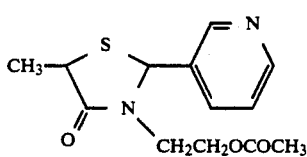

Pyridine (0.5 ml) was added to a solution of 3-(2-hydroxyethyl)-5-methyl-2-(3-pyridyl)thiazolidin-4-one (0.5 g, 2.1 mmol) in acetic anhydride (2 ml) under cooling with ice. This cooling with ice was further continued for 2 hours. The product mixture was concentrated by evaporation under reduced pressure, and subjected to medium-pressure chromatography (hexaneacetone), giving 3-(2-acetoxyethyl)-5-methyl-2-(3-pyridyl)-thiazolidin-4-one (0.45 g, 77% yield). NMR (CDCl₃) δ [ppm]; 1.62 (1 H, d, J=7.1 Hz), 1.66 (2 H, d, J=7.1 Hz), 2.06 (3 H, s), 5.74 (1 H, s). IR (CHCl₃) [cm⁻¹]; 2960, 1740, 1693, 1590, 1579, 1350, 1020.

EXAMPLE 14

Preparation of 3-t-butylocycarbonylmethyl-5-methyl-2-(3-pyridyl)-thiazolidin-4-one (compound Nos. 15, 16)

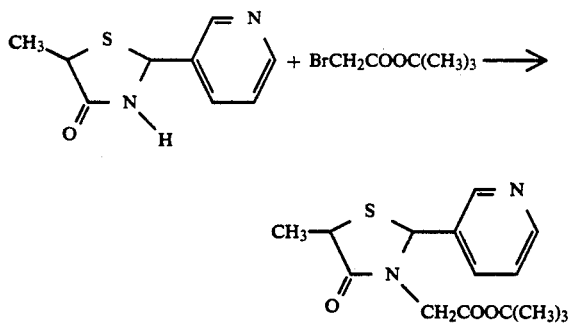

According to the procedure of Example 10, the trans-isomer (compound No. 15) and the cis-isomer (compound No. 16) of the title compound were prepared by using 5-methyl-2-(3-pyridyl)thiazolidin-4-one, t-butyl bromoacetate, and sodium hydride as charge stock. Compound No. 15: trans-isomer, m.p. 132°-133° C. IR (nujol) [cm⁻¹]; 1738, 1690, 1679, 1572, 1260, 1164 Compound No. 16: cis-isomer, m.p. 108°-108.5° C. IR (nujol) [cm⁻¹]; 1738, 1681, 1694, 1591, 1575, 1247, 1170.

EXAMPLE 15

Preparation of 3-(2-Acetylthioethyl)-5-methyl-2-(3-pyridyl)thiazolidin-4-one (compound Nos. 17, 18)

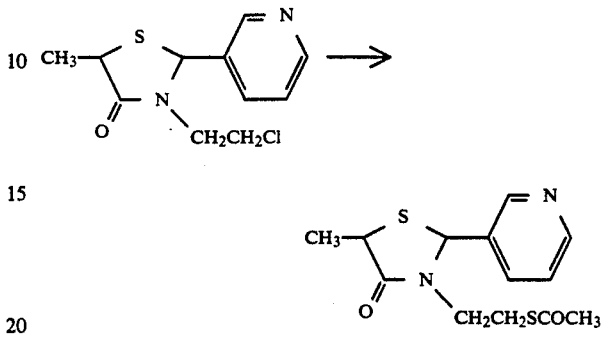

Potassium thioacetate (0.53 g, 4.7 mmol) was added to a solution of 2,5-trans-3-(2-chloroethyl)-5-methyl-2-(3-pyridyl)thiazolidin-4-one (1 g, 3.9 mmol) in dimethylformamide (5 ml) and the mixture was stirred for 1 hour under cooling with ice. The product mixture, after addition of aqueous NaHCO₃, was extracted with ethyl acetate. The extract was washed with aqueous NaCl, dried, and the solvent was removed in vacuo. The residue was chromatographed on silica gel, giving 2,5-trans-3-(2-acetylthioethyl)-5-methyl-2-(3-pyridyl)-thiazolidin-4-one (0.85 g, 78% yield).

The cis-isomer also was prepared as stated above. Compound No. 17: trans-isomer, m.p. 60°-62° C. Compound No. 18: cis-isomer, m.p. 55°-56.5° C.

EXAMPLE 16

Preparation of 5-(n-nonyl)-2-(3-pyridyl)thiazolidin-4-one (compound No. 19)

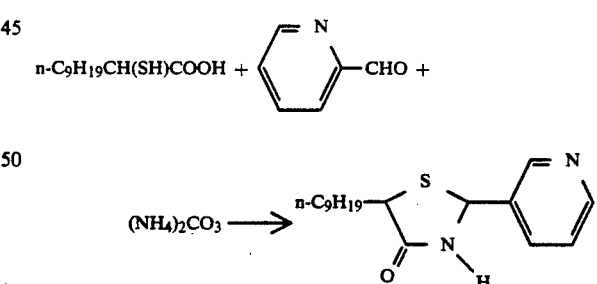

2-Mercaptoundecanoic acid (20 g, 91.6 mmol), nicotinaldehyde (8.64 ml, 91.6 mmol), and (NH₄)₂CO₃ (3.3 g, 34.3 mmol) were added to benzene (300 ml), and subjected to azeotropic dehydration for 2 hours. After the reaction mixture was cooled, (NH₄)₂CO₃ (3.3 g, 34.3 mmol) was added at 30°-40° C., and the mixture was subjected to azeotropic dehydration. Then the solvent was removed under reduced pressure. The residue was chromatographed on silica gel, and upon recrystallization from etherhexane, gave 5-(n-nonyl)-2-(3-pyridyl)-thiazolidin-4-one (16.7 g, 59% yield). m.p. 90°-95° C.

EXAMPLE 17

Preparation of
3-(2-hydroxyethyl)-5-(n-nonyl)-2-(3-pyridyl)thiazolidin-4-one (compound No. 20)

n-C$_9$H$_{19}$CH(SH)COOH +

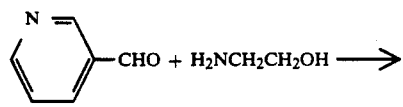

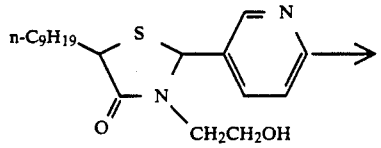

2-Mercaptoundecanoic acid (7 g, 32.1 mmol), nicotinaldehyde (3.03 ml, 32.1 mmol), and ethanolamine (1.93 ml, 32.1 mmol) were added to toluene, (100 ml) and subjected to azeotropic dehydration for 1 hour. The product mixture was cooled and evaporated under reduced pressure to remove the solvent. The residue was purified by column chromatography, giving 3-(2-hydroxyethyl)-5-(n-nonyl)-2-(3-pyridyl)thiazolidin-4-one (8.17 g, 73% yield). NMR (CDCl$_3$, δ) [ppm]; 0.85–0.9 (3 H, m), 2.9–3.01 (1 H, m), 3.65–3.80 (3 H, m), 3.97–4.01 (0.7 H, m), 4.02–4.07 (0.3 H, m), 5.78 (0.3 H, d, J=2.0 Hz), 5.80 (0.7 H, s).

EXAMPLE 18

Preparation of
3-(2-chloroethyl)-5-(n-nonyl)-2-(3-pyridyl)thiazolidin-4-one (compound Nos. 21, 22)

Triphenylphosphine (3.44 g, 13 mmol) was added to a mixture of 3-(2-hydroxyethyl)-5-(n-nonyl)-2-(3-pyridyl)thiazolidin-4-one (3.49 g, 10 mmol) and carbon tetrachloride (20 ml) with stirring at room temperature. Then the mixture was refluxed with stirring for 2.5 hours.

The product mixture was cooled and filtered to remove the formed crystals. The filtrate was concentrated and chromatographed, giving the cis-isomer (0.55 g) and trans-isomer (1.46 g) of the title compound and a mixture of two isomers (0.94 g) (total 2.95 g, 80% yield). cis-Isomer (compound No. 21) IR (CHCl$_3$) [cm$^{-1}$]; 2915. 2850, 1675, 1590, 1580, 1350. NMR (δ, CDCl$_3$, ppm); 2.99 (1 H, ddd, J=14.52, 7.92 and 5.28 Hz), 3.49 (1 H, dt, J=11.55 and 5.28 Hz), 3.72 (1 H, ddd, J=11.55, 7.92 and 5.28 Hz), 3.95 (1 H, dt, J=14.52 and 5.28 Hz), 4.01 (1 H, dd, J=9.90 and 2.97 Hz), 5.86 (1 H, s). trans-isomer (compound No. 22) IR (CHCl$_3$) [cm$^{-1}$]; 2920, 2850, 1678, 1590, 1580, 1355. NMR (δ, CDCl$_3$, ppm); 2.97 (1 H, ddd, J=14.52, 8.24 and 4.95 Hz), 3.51 (1 H, ddd, J=11.54, 5.28 and 4.95 Hz), 3.74 (1 H, ddd, 11.54 8.24 and 4.95 Hz), 3.98 (1 H, ddd, J=9.90, 3.63 and 1.64 Hz), 5.85 (1 H, d, J=1.64 Hz).

EXAMPLE 19

Preparation of
3-(2-dimethylaminoethyl)-5-(n-nonyl)-2-(3-pyridyl)-thiazolidin-4-one (compound No. 23)

n-C$_9$H$_{19}$CH(SH)COOH +

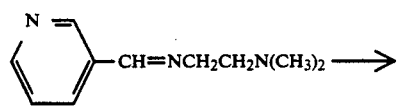

2-Mercaptoundecanoic acid (2 g, 9.16 mmol) and N-nicotinylidene-N',N'-dimethylethylenediamine (1.62 g, 9.16 mmol) were dissolved in toluene (50 ml), and subjected to azeotropic dehydration for 2 hours. The solvent was removed from the product mixture by evaporation under reduced pressure. The residue was purified by column chromatography, giving 3-(2-dimethylaminoethyl)-5-(n-nonyl)-2-(3-pyridyl)thiazolidin-4-one (3.1 g, 90% yield). IR (CHCl$_3$) [cm$^{-1}$]; 2850, 1660, 1577, 1408.

EXAMPLE 20

Preparation of
3-(2-dimethylaminoethyl)-5-(n-nonyl)-2-(3-pyridyl)-thiazolidin-4-one (compound No. 23)

n-C$_9$H$_{19}$CH(SH)COOH +

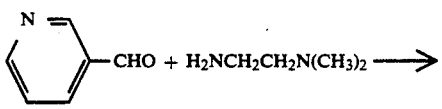

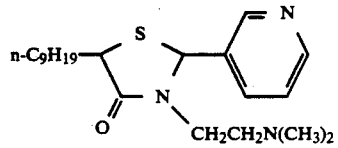

2-Mercaptoundecanoic acid (5.0 g, 22.9 mmol), pyridine-3-aldehyde (2.16 ml, 22.9 mmol), and N-dimethylaminoethylamine (2.51 ml, 22.9 mmol) were dissolved in toluene (100 ml), and subjected to azeotropic dehydration for 2 hours. The solvent was removed from the product mixture by evaporation under reduced pressure. The residue was purified by column chromatography, giving 3-(2-dimethylaminoethyl)-5-(n-nonyl)-2-(3-pyridyl)thiazolidin-4-one (7.9 g, 91% yield). IR (CHCl$_3$) [cm$^{-1}$]; 2850, 1660, 1577, 1408.

EXAMPLE 21

Preparation of 5-ethyl-3-(2-dimethylaminoethyl)-2-(3-pyridyl)thiazolidin-4-one (compound No. 24)

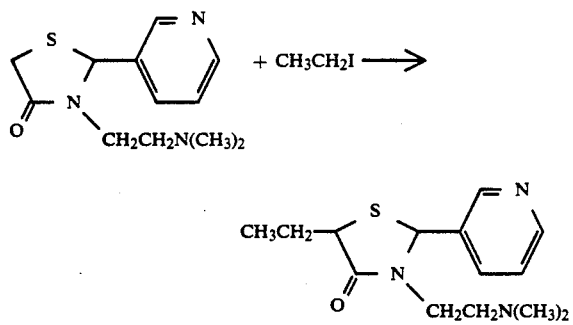

n-Butyllithium solution (5 ml, 8 mmol) in hexane was added dropwise to a solution of diisopropylamine (1.42 ml, 7.96 mmol) in dry tetrahydrofuran at −30° to −40° C. The mixture was kept between those temperatures for 1 hour and then cooled to −78° C. Thereto was added dropwise a solution of 3-(2-dimethylaminoethyl)-2-(3-pyridyl)thiazolidin-4-one (2 g, 7.96 mmol) in dry tetrahydrofuran (10 ml). This reaction mixture was kept at that temperature for 1 hour. Then, ethyl iodide (1.24 g, 7.96 mmol) was added, and this reaction mixture was slowly warmed up to room temperature and maintained there for 30 minutes. The resulting mixture, after addition of aqueous NaCl, was extracted with ethyl acetate. The extract was washed with aqueous NaCl, dried, and concentrated by evaporation under reduced pressure. The residue was purified by column chromatography, giving 5-ethyl-3-(2-dimethylaminoethyl)-2-(3-pyridyl)-thiazolidin-4-one (1.84 g, 83% yield). NMR (CDCl, δ) [ppm]; 1.06 (3 H, t, J=7.3 Hz), 2.15 (6 H, s), 3.75–3.85 (1 H, m), 4.00–4.05 (1 H, m), 5.86 (1 H, d, J=2.0 Hz).

EXAMPLE 22

Preparation of 5,5-dimethyl-3-(2-dimethylaminoethyl)-2-(3-pyridyl)-thiazolidin-4-one (compound No. 25)

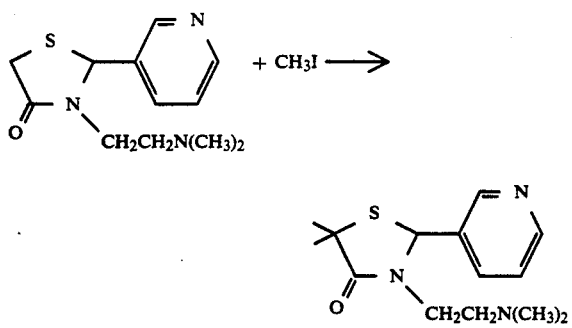

A n-butyllithium solution (10 ml, 16 mmol) in hexane was added to dropwise to a solution of diisopropylamine (2.84 ml, 15.9 mmol) in dry tetrahydrofuran (6 ml) at −20° to −30° C. The mixture was kept between those temperatures for 1 hour and then cooled to −78° C. Thereto was added dropwise a solution of 3-(2-dimethylaminoethyl)-2-(3-pyridyl)thiazolidin-4-one (2 g, 7.96 mmol) in dry tetrahydrofuran (10 ml). The resulting mixture was kept at −78° C. for 1 hour. After addition of methyl iodide (2.26 g, 15.9 mmol), this reaction mixture was slowly warmed up to the room temperature and allowed to stand overnight. The resulting mixture, after addition of aqueous NaCl, was extracted with ethyl acetate. The extract was washed with aqueous NaCl, dried, and the solvent was removed in vacuo. The residue was purified by column chromatography, giving 5,5-dimethyl-3-(2-dimethylaminoethyl)-2-(3-pyridyl)thiazolidin-4-one (257 mg, 12% yield). m.p. 67°–70° C.

EXAMPLE 23

Preparation of 3-(2-dimethylaminoethyl)-5-(n-nonyl)-2-(3-pyridyl)-thiazolidin-4-one (compound No. 23)

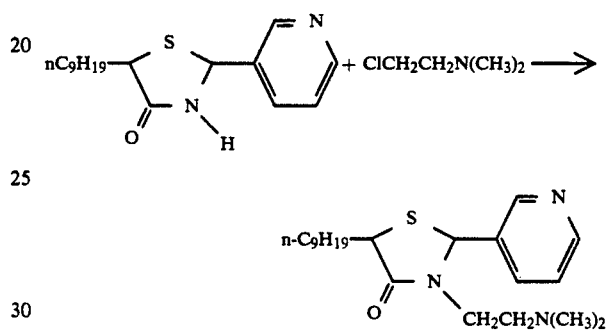

$K_2CO_3$ (0.9 g, 6.52 mmol) and 2-dimethylaminoethyl chloride hydrochloride (0.47 g, 3.26 mmol) were added to a solution of 5-(n-nonyl)-2-(3-pyridyl)-thiazolidin-4-one (1 g, 3.26 mmol) in dry dimethylformamide (10 ml). The mixture was kept at 50° C. for 10 hours. The resulting mixture, after addition of aqueous NaCl, was extracted with ethyl acetate. The extract was washed with aqueous NaCl, dried, and the solvent was removed in vacuo. The residue was purified by chromatography on silica gel, giving 3-(2-dimethylaminoethyl)-5-(n-nonyl)-2-(3-pyridyl)thiazolidin-4-one (0.41 g, 33% yield). IR ($CHCl_3$) [cm$^{-1}$]; 2850, 1660, 1578, 1407.

EXAMPLE 24

Preparation of 3-(2-acetylaminoethyl)-2-(3-pyridyl)-5-(n-nonyl)-thiazolidin-4-one (compound No. 26)

Acetic anhydride (0.2 g) was added dropwise to a solution of 3-(2-aminoethyl)-5-(n-nonyl)-2-(3-pyridyl)-thiazolidin-4-one (0.50 g, 1.43 mmol) in pyridine (2 ml) with stirring under cooling with ice. The mixture was left standing overnight at room temperature. To this solution was added saturated aqueous $NaHCO_3$ (30 ml), and the mixture was extracted with benzene. After drying of the extract, the solvent was removed therefrom by evaporation under reduced pressure, giving the intended 3-(2-acetylaminoethyl)-5-(n-nonyl)-2-(3-pyridyl)thiazolidin-4-one (0.52 g, 92% yield) in oily form. IR ($CHCl_3$) [cm$^{-1}$]; 3430, 2920, 2850, 1665, 1590, 1580, 1365. NMR (δ, $CDCl_3$ ppm); 1.95 (3 H, s), 3.93 (0.45 H, dd, 990 and 3.63 Hz), 4.03 (0.55 H, ddd, 9.24, 3.63 and 1.65 Hz), 5,75 (0.55 H, d, 1.65 Hz), 5.76 (0.45 H, s), 6.06–6.11 (1 H, m).

EXAMPLE 25

Preparation of 3-(2-dimethylaminoethyl)-5-(n-nonyl)-2-(3-pyridyl)-thiazolidin-4-one (trans-isomer) (compound No. 27)

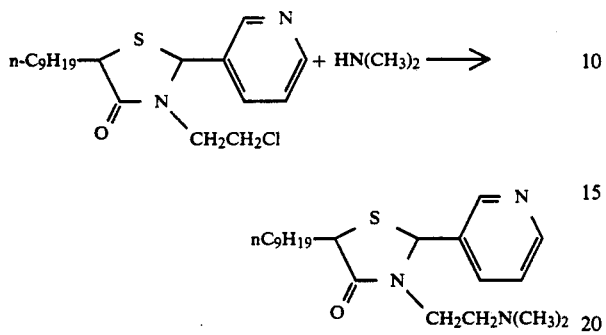

A 50% aqueous dimethylamine solution (1.0 ml, 11 mmol) was added to a solution of trans-isomer (128 mg, 0.35 mmol) of 3-(2-chloroethyl)-5-(n-nonyl)-2-(3-pyridyl)thiazolidin-4-one in dimethylsulfoxide (3 ml). The mixture, placed in a sealed tube, was heated at 100° C. for 2 hours. After removal of the solvent by evaporation under reduced pressure, the residue was dissolved in chloroform (30 ml). The solution was washed twice with saturated aqueous NaHCO$_3$ and dried. Removal of the chloroform gave the intended trans-isomer (131 mg, 100% of theoretical) of 3-(2-dimethylaminoethyl)-5-(n-nonyl)-2-(3-pyridyl)thiazolidin-4-one in oily form. IR (CHCl$_3$) [cm$^{-1}$]; 2930, 2860, 1670, 1580, 1355. NMR ($\delta$, CDCl$_3$, ppm); 2.15 (6 H, s), 2.24 (1 H, dt, 12.87 and 5.61 Hz), 2.46 (1 H, ddd, 12.87, 7.20 and 5.94 Hz), 2.69 (1 H, ddd, 14.19, 7.20 and 5.61 Hz), 3.80 (1 H, ddd, 14.19, 5.94 and 5.61 Hz), 4.03 (1 H, ddd, 8.58, 3.96 and 1.98 Hz), 5.86 (1 H, d, 1.98 Hz).

EXAMPLE 26

Isolation-Purification of trans-isomer and cis-isomer 3-(2-Dimethylaminoethyl)-5-(n-nonyl)-2-(3-pyridyl)-thiazolidin-4-one (7.9 g) prepared in Example 2 was subjected to medium-pressure liquid chromatography (column size: 40 mm × 500 mm, Silica gel-60 ®, carrier : hexane : ethanol : aqueous ammonia = 3000:300:50), giving the trans-isomer (1.42 g), the cis-isomer (3.42 g), and their mixture (2.77 g). trans-isomer (compound No. 27) IR (CHCl$_3$) [cm$^{-1}$]; 2930, 2860, 1670, 1580, 1355. NMR ($\delta$, CDCl$_3$ ppm); 2.15 (6 H, s), 40–40.6 (1 H, m), 5.86 (1 H, d, J=2.0 Hz). cis-isomer (compound No. 28) IR (CHCl$_3$) [cm$^{-1}$]; 2930, 2860, 1670, 1590, 1360. NMR ($\delta$, CDCl$_3$ ppm); 2.13 (6 H, s), 3.97 (1 H, dd, J=3.7 and 9.8 Hz), 5.84 (1 H, s).

A 5% HCl-isopropanol mixture (5 g, 7 mmol) was added to a portion of (1 g, 2.65 mmol) of the obtained trans-isomer, and stirred for 1 hour at room temperature. The solvent was removed by evaporation under reduced pressure. The residue, subjected to recrystallization from a 1:3 ethanol-hexane mixture (5 ml), gave the hydrochloride of the trans-isomer (compound No. 173) (1.02 g, 85% yield). m.p. 175.5°–178° C. IR (KBr) [cm$^{-1}$]; 2920, 2850, 2660, 1670, 1460.

EXAMPLE 27

Preparation of 3-dimethylaminoethyl-5-(3-hydroxypropyl)-2-(3-pyridyl)thiazolidin-4-one (compound No. 129).

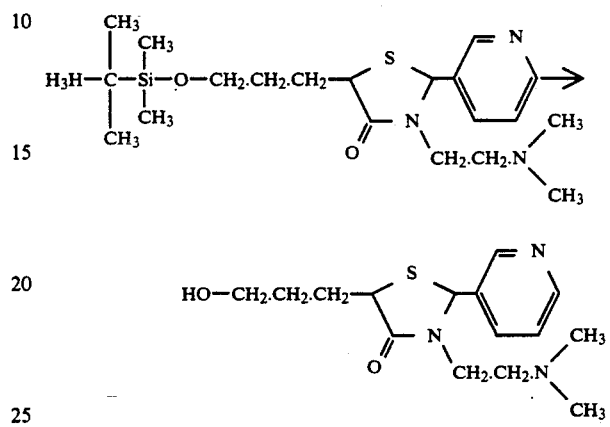

A 1M solution (15 ml) of tetrabutylammonium fluoride in tetrahydrofuran was added dropwise to a solution of 3-dimethylaminoethyl-5-(3-t-butyldimethyl-silyloxypropyl)-2-(3-pyridyl)thiazolidin-4-one (2.6 g, 6.02 mmol) of dry tetrahydrofuran (12 ml) under cooling with ice. Then the mixture was stirred at room temperature for 2 hours to complete the reaction. Saturated aqueous NaHCO$_3$ (10 ml) was added dropwise to the product mixture, and the resulting aqueous layer was extracted 6 times with ethyl acetate. The extract was dried over MgSO$_4$, and the solvent was removed under reduced pressure. The residual crude product was purified by medium-pressure liquid chromatography (Si-60 ® Art. 9385, eluent : hexane : ethanol : aqueous ammonia = 3000:400:50), giving 3-dimethylaminoethyl-5-(3-hydroxypropyl)-2-(3-pyridyl)thiazolidin-4-one (1.7 g, 88% yield). IR (CHCl$_3$) [cm$^{-1}$]; 3400 (br), 1670, 1595, 1580, 1360. NMR (CDCl$_3$) [$\delta$ ppm]; 2.16 (6 H, s), 4.10–4.15 (1 H, m), 5.86 (1 H, d, J=2 Hz).

EXAMPLE 28

Compounds shown in the following table were prepared according to the procedure of Examples 1–26. In the table, R$^1$, R$^2$ and R$^3$ are substituents shown in the following formula:

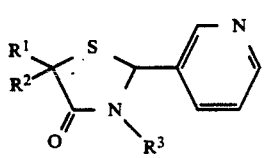

In the row of "Configuration" in the table, "trans" means that the 2- and 5-positional substituents on the thiazolidin-4-one ring are in the configuration of trans to each other; "cis" means that these substituents are in the configuration of cis to each other; and m means a trans-cis mixture.

| Compound No. | $R_1$ | $R_2$ | $R_3$ | Configuration |
|---|---|---|---|---|
| 29 | H | H | (CH₂)₂-[3,4-dimethoxyphenyl] | — |
| 30 | CH₃ | " | CH₂CH₃ | m |
| 31 | " | " | CH₂CH=CH₂ | trans |
| 32 | " | " | " | cis |
| 33 | " | " | CH₂C≡CH | trans |
| 34 | " | " | " | cis |
| 35 | " | " | (CH₂)₂-phenyl | trans |
| 36 | " | " | " | cis |
| 37 | " | " | (CH₂)₂-[3,4-dimethoxyphenyl] | trans |
| 38 | " | " | (CH₂)₂-[3,4-dimethoxyphenyl] | cis |
| 39 | CH₃ | H | (CH₂)₃OCH₃ | m |
| 40 | " | " | CH₂CON(CH₃)₂ | trans |
| 41 | " | " | " | cis |
| 42 | CH₂CH₃ | " | CH₃ | m |
| 43 | (CH₂)₂CH₃ | " | " | m |
| 44 | CH₂CH(CH₃)₂ | " | " | m |
| 45 | CH(CH₃)CH₂CH₃ | " | " | m |
| 46 | (CH₂)₄CH₃ | " | " | m |
| 47 | (CH₂)₅CH₃ | " | " | m |
| 48 | (CH₂)₈CH₃ | " | " | m |
| 49 | " | " | " | trans |
| 50 | " | " | " | cis |
| 51 | (CH₂)₉CH₃ | " | " | m |
| 52 | (CH₂)₈CH₃ | " | (CH₂)₂-[3,4-dimethoxyphenyl] | trans |
| 53 | " | " | " | cis |
| 54 | (CH₂)₈CH₃ | H | CH₂COOC₂H₅ | trans |
| 55 | " | " | " | cis |
| 56 | " | " | (CH₂)₂COOC₂H₅ | trans |
| 57 | " | " | " | cis |
| 58 | (CH₂)₁₅CH₃ | " | (CH₂)₂-[3,4-dimethoxyphenyl] | trans |
| 59 | " | " | " | cis |
| 60 | CH₂-cyclohexyl | " | CH₃ | m |

-continued

| Compound No. | R₁ | R₂ | R₃ | Configuration |
|---|---|---|---|---|
| 61 | CH₂—C₆H₅ (benzyl) | " | " | m |
| 62 | (CH₂)₂CH₃ | (CH₂)₂CH₃ | " | |
| 63 | CH₂CH=CH₂ | H | " | m |
| 64 | CH₂C≡CH | " | " | m |
| 65 | CH₃ | H | CH₂CH₂CH₂N(CH₃)₂ | trans |
| 66 | " | " | " | cis |
| 67 | n-C₃H₇ | H | CH₂CH₂N(CH₃)₂ | trans |
| 68 | " | " | " | cis |
| 69 | n-C₄H₉ | " | " | trans |
| 70 | " | " | " | cis |
| 71 | n-C₅H₁₁ | " | " | trans |
| 72 | " | " | " | cis |
| 73 | n-C₆H₁₃ | " | " | trans |
| 74 | " | " | " | cis |
| 75 | n-C₇H₁₅ | " | " | trans |
| 76 | " | " | " | cis |
| 77 | n-C₈H₁₇ | " | " | trans |
| 78 | " | " | " | cis |
| 79 | n-C₁₀H₂₁ | " | " | trans |
| 80 | " | " | " | cis |
| 81 | n-C₁₁H₂₃ | " | " | trans |
| 82 | " | " | " | cis |
| 83 | n-C₁₂H₂₅ | H | CH₂CH₂N(CH₃)₂ | trans |
| 84 | " | " | " | cis |
| 85 | n-C₁₃H₂₇ | " | " | trans |
| 86 | " | " | " | cis |
| 87 | n-C₁₄H₂₉ | " | " | trans |
| 88 | " | " | " | cis |
| 89 | n-C₁₅H₃₁ | " | " | trans |
| 90 | " | " | " | cis |
| 91 | n-C₁₆H₃₃ | " | " | trans |
| 92 | " | " | " | cis |
| 93 | n-C₁₇H₃₅ | " | " | trans |
| 94 | " | " | " | cis |
| 95 | n-C₁₈H₃₇ | " | " | trans |
| 96 | " | " | " | cis |
| 97 | n-C₁₉H₃₉ | " | " | trans |
| 98 | " | " | " | cis |
| 99 | n-C₂₀H₄₁ | H | CH₂CH₂N(CH₃)₂ | trans |
| 100 | " | " | " | cis |
| 101 | CH₃ | " | CH₂CH₂N(morpholino) | trans |
| 102 | " | " | " | cis |
| 103 | n-C₃H₇ | " | CH₂CH₂CH₂N(CH₃)₂ | trans |
| 104 | " | " | " | cis |
| 105 | n-C₆H₁₃ | " | " | trans |
| 106 | " | " | " | cis |
| 107 | n-C₉H₁₉ | " | " | trans |
| 108 | " | " | " | cis |
| 109 | n-C₁₆H₃₃ | " | " | trans |
| 110 | " | " | " | cis |
| 111 | n-C₁₈H₃₇ | " | " | trans |
| 112 | " | " | " | cis |
| 113 | CH₃ | CH₃ | " | — |
| 114 | n-C₉H₁₉ | H | CH₂(CH₂)₂CH₂N(CH₃)₂ | m |
| 115 | n-C₉H₁₉ | H | CH₂CH₂N(C₂H₅)₂ | trans |
| 116 | " | " | " | cis |
| 117 | " | " | CH₂CH₂N(C₂H₅)(H) | trans |
| 118 | " | " | " | cis |
| 119 | " | " | CH₂CH₂N(pyrrolidino) | m |

-continued

| Compound No. | R₁ | R₂ | R₃ | Configuration |
|---|---|---|---|---|
| 120 | " | " | CH₂CH₂N⟨piperazine⟩NH | m |
| 121 | " | " | CH₂CH₂NH₂ | m |
| 122 | " | " | CH₂CH₂N(C₂H₅)(COCH₃) | m |
| 123 | (CH₃)₂CH(CH₂)₃CHCH₃(CH₂)₂ | " | CH₂CH₂N(CH₃)₂ | trans |
| 124 | CH₂=CHCH₂ | " | " | trans |
| 125 | C₆H₅CH₂ | " | " | trans |
| 126 | (CH₃)₂CH₂CH₂CH₂ | " | " | trans |
| 127 | CH₃ | " | " | trans |
| 128 | " | " | " | cis |
| 130 | C₆H₅CH₂O(CH₂)₂ | C₆H₅CH₂O(CH₂)₂ | —CH₂CH₂N(CH₃)₂ | — |
| 131 | C₆H₅CH₂O(CH₂)₂ | H | " | trans |
| 132 | CH₃(CH₂)₃O(CH₂)₂ | CH₃(CH₂)₃O(CH₂)₂ | —CH₂CH₂N(CH₃)₂ | — |
| 133 | CH₃(CH₂)₃O(CH₂)₂ | H | CH₂CH₂N(CH₃)₂ | trans |
| 134 | CH₃(CH₂)₃O(CH₂)₂O(CH₂)₂ | CH₃(CH₂)₃O(CH₂)₂O(CH₂)₂ | —CH₂CH₂N(CH₃)₂ | — |
| 135 | CH₃(CH₂)₃O(CH₂)₂O(CH₂)₂ | H | —CH₂CH₂N(CH₃)₂ | trans |
| 136 | Hydrochloride of No. 135 | | | |
| 137 | CH₃CH₂O(CH₂)₃— | H | —CH₂CH₂N(CH₃)₂ | m |
| 138 | Hydrochloride of No. 137 | | | |
| 139 | CH₂=CH₂CH₂O(CH₂)₂— | CH₂=CH₂CH₂O(CH₂)₂— | —CH₂CH₂N(CH₃)₂ | |
| 140 | CH₂=CH₂CH₂O(CH₂)₂ | H | —CH₂CH₂N(CH₃)₂ | m |
| 141 | HO(CH₂)₂O(CH₂)₂— | H | —CH₂CH₂N(CH₃)₂ | m |
| 142 | (CH₃)₂CHCH₂O(CH₂)₂ | (CH₃)₂CHCH₂O(CH₂)₂ | —CH₂CH₂N(CH₃)₂ | — |
| 143 | (CH₃)₂CHCH₂O(CH₂)₂ | H | —CH₂CH₂N(CH₃)₂ | m |
| 144 | Hydrochloride of No. 143 | | | |
| 145 | (CH₃)₃CO(CH₂)₂— | H | —CH₂CH₂N(CH₃)₂ | m |
| 146 | CH₃(CH₂)₂O(CH₂)₂O(CH₂)₂ | CH₃(CH₂)₂O(CH₂)₂O(CH₂)₂ | CH₂CH₂N(CH₃)₂ | — |
| 147 | CH₃(CH₂)₂O(CH₂)₂O(CH₂)₂ | H | CH₂CH₂N(CH₃)₂ | m |
| 148 | Hydrochloride of No. 147 | | | |
| 149 | (CH₃)₂CHCH₂O(CH₂)₂O(CH₂)₂ | (CH₃)₂CHCH₂O(CH₂)₂O(CH₂)₂ | CH₂CH₂N(CH₃)₂ | — |
| 150 | (CH₃)₂CHCH₂O(CH₂)₂O(CH₂)₂ | H | CH₂CH₂N(CH₃)₂ | trans |
| 151 | Hydrochloride of No. 150 | | | |
| 152 | (CH₃)₂CHO(CH₂)₂O(CH₂)₂ | H | CH₂CH₂N(CH₃)₂ | m |
| 153 | (CH₃)₂CHO(CH₂)₂ | (CH₃)₂CHO(CH₂)₂ | CH₂CH₂N(CH₃)₂ | — |
| 154 | (CH₃)₂CHO(CH₂)₂ | H | CH₂CH₂N(CH₃)₂ | m |
| 155 | CH₃O(CH₂)₂O(CH₂)₂ | H | CH₂CH₂N(CH₃)₂ | m |
| 156 | (CH₃)₂CHO(CH₂)₂O(CH₂)₂ | H | CH₂CH₂N(CH₃)₂ | trans |
| 157 | Hydrochloride of No. 156 | | | |
| 158 | CH₃CH₂O(CH₂)₂O(CH₂)₂ | CH₃CH₂O(CH₂)₂O(CH₂)₂ | CH₂CH₂N(CH₃)₂ | |
| 159 | CH₃CH₂O(CH₂)₂O(CH₂)₂ | H | CH₂CH₂N(CH₃)₂ | m |
| 160 | Hydrochloride of No. 159 | | | |
| 161 | CH₃CH₂O(CH₂)₂O(CH₂)₂ | CH₃CH₂O(CH₂)₂O(CH₂)₂ | CH₂CH₂N(CH₃)₂ | — |
| 162 | CH₃CH₂O(CH₂)₂O(CH₂)₂ | H | CH₂CH₂N(CH₃)₂ | trans |
| 163 | Hydrochloride of No. 162 | | | |
| 164 | (CH₃)₃C(CH₂)₂SiO(CH₂)₂O(CH₂)₂ | (CH₃)₃C(CH₂)₂SiO(CH₂)₂O(CH₂)₂ | CH₂CH₂N(CH₃)₂ | — |
| 165 | (CH₃)₃C(CH₂)₂Sio(CH₂)₂O(CH₂)₂ | H | CH₂CH₂N(CH₃)₂ | m |
| 166 | (CH₃)₃C(CH₂)₂SiO(CH₂)₂ | (CH₃)₃C(CH₂)₂SiO(CH₂)₂ | CH₂CH₂N(CH₃)₂ | |
| 167 | (CH₃)₃C(CH₃)₂SiO(CH₂)₂ | H | CH₂CH₂N(CH₃)₂ | m |
| 168 | (CH₃)₃C(CH₃)₂SiO(CH₂)₃ | (CH₃)₃C(CH₃)₂SiO(CH₂)₃ | CH₂CH₂N(CH₃)₂ | m |
| 169 | (CH₃)₃C(CH₃)₂SiO(CH₂)₃ | H | CH₂CH₂N(CH₃)₂ | trans |
| 170 | (CH₃)₃C(CH₃)₂SiO(CH₂)₃ | H | CH₂CH₂N(CH₃)₂ | cis |
| 171 | CF₃CH₂ | H | CH₂CH₂N(CH₃)₂ | m |
| 172 | CF₃(CF₂)₂CH₂CH₂ | H | CH₂CH₂N(CH₃)₂ | trans |

| Compound No. | R₁ | R₂ | R₃ | Configuration |
|---|---|---|---|---|
| 174 | Hydrochloride of No. 73 | | | |
| 175 | Hydrochloride of No. 75 | | | |
| 176 | Hydrochloride of No. 77 | | | |
| 177 | Hydrochloride of No. 79 | | | |

| Compound No. | M.P. or NMR($\delta$, CDCl₃)[PPM] | a) IR(CHCl₃)[cm⁻¹]<br>b) IR(nujol)[cm⁻¹] |
|---|---|---|
| 29 | 2.5–3.0(3H, m), 3.6–4.0(3H, m), 3.85(3H, s), 3.88(3H, s), 5.23(1H, d, J=1.5Hz) | a) 2940, 2845, 1675, 1595, 1440, 1360, 1020. |
| 30 | 0.99–1.08(3H, m), 1.59–1.67(3H, m), 3.6–3.85(1H, m), 3.9–4.05(0.6H, m), 4.05–4.20(0.4H, m), 5.61(0.4H, d, J=1.7Hz), 5.63(0.6H, s). | a) 2930, 1670, 1585, 1575, 1445, 1419, 1120. |
| 31 | 1.63(3H, d, J=7.1Hz), 3.0–3.2(1H, m), 4.0–4.2(1H, m), 4.4–4.6(1H, m), 5.0–5.3(2H, m), 5.57(1H, d, J=2Hz), 5.6–5.8(1H, m). | a) 1674, 1590, 1579, 1120. |
| 32 | 46–48° C. | b) 1650, 1595, 1580, 1275, 1180, 1021. |
| 33 | 1.63(3H, d, J=7.1Hz), 3.26–3.34(1H, m), 4.06–4.12(1H, m), 4.61–4.70(1H, m), 5.80(1E, d, J=1.7Hz). | a) 3405, 1680, 1578, 1400, 1348. |
| 34 | 1.67(3H, d, J=7.1Hz), 3.23–3.30(1H, m), 3.96–4.05(1H, m), 4.61–4.69(1H, m), 5.80(1H, s). | a) 3405, 1680, 1578, 1400, 1350. |
| 35 | 111–111.5° C. | b) 1660, 1580, 1418, 1305, 1149, 1025, 1005. |
| 36 | 107–107.5° C. | b) 1664, 1649, 1579, 1420, 1305, 1157. |
| 37 | 92–93° C. | b) 1662, 1576, 1512, 1420, 1269, 1239, 1142, 1025. |
| 38 | 92–94° C. | b) 1658, 1585, 1511, 1416, 1260, 1140, 1021. |
| 39 | 1.59–1.67(3H, m), 3.26(1.8H, s), 3.29(1.2H, s), 5.63(0.4H, d, J=1.7Hz), 5.65(0.6H, s). | a) 2920, 2860, 1760, 1572, 1440, 1300, 1111. |
| 40 | 104–106° C. | b) 1677, 1650, 1580, 1299, 1145, 1025, 710. |
| 41 | 100–101° C. | b) 1681, 1656, 1591, 1580, 1140. |
| 42 | 1.0–2.4(5H, m), 2.73(1H, s), 2.74(1H, s), 3.9–4.2(1H, m), 5.48(0.7H, d, J=2.0Hz), 5.50(0.3H, s). | a) 2950, 1670, 1590, 1578, 1388, 1301, 1020. |
| 43 | 0.9–2.4(7H, m), 2.72(1.2H, s), 2.75(1.8H, s), 3.9–4.1(1H, m), 5.47(0.6H, d, J=2.0Hz), 5.49(0.4H, s). | a) 2960, 2940, 1670, 1595, 1581, 1392, 1015. |
| 44 | 0.9–2.4(8H, m), 2.72(3H, s), 4.1–4.3(1H, m). | a) 2955, 1672, 1590, 1579, 1305. |
| 45 | 0.8–2.5(8H, m), 5.47(0.5H, d, J=2.0Hz), 5.49(0.5H, s). | a) 2950, 1674, 1589, 1578. |
| 46 | 0.8–2.3(11H, m), 2.72(0.3H, s), 2.74(2.7H, s), 3.9–4.1(1H, m), 5.47(0.9H, d, J=1.7Hz), 5.49(0.1H, s). | a) 2930, 2855, 1670, 1590, 1578, 1390, 1120, 1009. |
| 47 | 0.8–2.3(13H, m), 2.72(0.6H, s), 2.74(2.4H, s), 3.9–4.1(1H, m), 5.47(0.8H, d, J=2.0Hz), 5.49(0.2H, s). | a) 2925, 2855, 1670, 1589, 1578, 1390, 1300, 1020. |
| 48 | 0.8–2.4(19H, m), 2.72(1H, s), 2.74(2H, s), 3.9–4.1(1H, m), 5.47(0.74H, d, J=2.0Hz), 5.49(0.3H, s). | a) 2920, 2850, 1670, 1589, 1576, 1300, 1009. |
| 49 | 52.5–53° C. | b) 1663, 1578, 1420, 1020. |
| 50 | 67.5–68.5° C. | b) 1660, 1575, 1408, 1391, 1325, 1250, 708. |
| 51 | 0.8–2.4(21H, m), 2.72(1H, s), 2.74(2H, s), 3.9–4.1(1H, m), 5.47(0.7H, d, J=2.0Hz), 5.49(0.3H, s). | a) 2920, 2850, 1670, 1590, 1578, 1300, 1010. |
| 52 | 3.86(3H, s), 3.87(3H, s), 5.17(1H, d, J=1.7Hz). | a) 2930, 2860, 1670, 1590, 1360. |
| 53 | 3.84(3H, s), 3.87(3H, s), 5.20(1H, s). | a) 2920, 2850, 1670, 1589, 1138, 1018. |

-continued

| | | |
|---|---|---|
| 54 | 57–58° C. | b) 1724, 1693, 1579, 1432, 1292, 1023, 715. |
| 55 | 47–48° C. | b) 1742, 1683, 1577, 1420, 1295, 1210, 1025, 709. |
| 56 | 55–56° C. | b) 1739, 1660, 1550, 1214. |
| 57 | 46–47° C. | b) 1740, 1667, 1657, 1582, 1191, 1020. |
| 58 | 55–56° C. | b) 1673, 1590, 1414, 1267, 1239, 1025, 800. |
| 59 | 77–78° C. | b) 1675, 1586, 1512, 1253, 1021. |
| 60 | (3H, s), 4.01(0.85H, dd, J=3.5 and 11.3Hz), 4.05–4.2(0.15H, m), 5.4–5.5(1H, m). | b) 1665, 1585, 1570, 1310, 1265, 1025. |
| 61 | 78–79° C. | b) 1660, 1578, 1262, 1025, 735. |
| 62 | 0.9–1.1(6H, m), 1.1–2.1(8H, m), 2.69(3H, s), 5.39(1H, s). | a) 2950, 2930, 1673, 1589, 1578, 1388, 901. |
| 63 | 2.72(0.75H, s), 2.75–(2.25H, s), 4.03–4.09(0.25H, m), 4.10–4.17(0.75H, m), 5.46(0.75H, d, J=2.0Hz), 5.50(0.25H, s). | a) 2900, 1675, 1590, 1580, 1390, 1350, 1300. |
| 64 | 133–135° C. | b) 3220, 1679, 1581, 1315, 1024, 721. |
| 65 | 81.5–82.5° C. | b) 2760, 1660, 1580, 1419, 1276, 1220, 1063, 847. |
| 66 | 73–74° C. | b) 1662, 1647, 1577, 1420, 1327, 1305, 1165, 1039, 1020. |
| 67 | 0.98(3H, t, J=7.3Hz), 2.15(6H, s), 2.35–2.55(1H, m), 3.7–3.9(1H, m), 4.0–4.1(1H, m) 5.86(1H, d, J=1.7Hz) | a) 1670, 1578, 1355, 1010. |
| 68 | 65–66° C. | b) 1659, 1585, 1419, 1291, 1260, 1021. |
| 69 | 0.94(3H, t, J=6.6Hz), 2.15(6H, s), 2.4–2.52(1H, m), 2.64–2.74(1H, m), 3.75–3.85(1H, m), 4.00–4.06(1H, m), 5.86(1H, d, J=2.0Hz) | a) 2930, 2790, 1665, 1580, 1360, 1098. |
| 70 | 0.92(3H, t, J=7.0Hz), 2.13(6H, s), 2.37–2.54(1H, m), 2.64–2.74(1H, m), 3.75–3.85(1H, m), 3.95–4.0(1H, m), 5.85(1H, s) | a) 2920, 2780, 1665, 1579, 1357, 1096. |
| 71 | 0.90(3H, t, J=7.0Hz), 2.15(6H, s), 2.39–2.51(1H, m), 2.64–2.74(1H, m), 3.75–3.85(1H, m), 4.0–4.06(1H, m), 5.86(1H, d, J=2.0Hz) | a) 2920, 2770, 1662, 1577, 1358. |
| 72 | 0.89(3H, t, J=7.0Hz), 2.13(6H, s), 2.38–2.54(1H, m), 2.64–2.74(1H, m), 3.75–3.85(1H, m), 3.95–4.00(1H, m), 5.84(1H, s) | a) 2920, 2770, 1662, 1577, 1358. |
| 73 | 0.89(3H, t, J=6.7Hz), 2.15(6H, s), 2.35–2.55(1H, m), 2.6–2.8(1H, m), 3.7–3.9(1H, m), 4.0–4.1(1H, m), 5.86(1H, d, J=2.0Hz) | a) 2930, 1664, 1578, 1358, 1295. |
| 74 | 0.88(3H, t, J=6.7Hz), 2.13(6H, s), 2.35–2.55(1H, m), 2.6–2.8(1H, m), 3.7–3.9(1H, m), 3.9–4.05(1H, m), 5.84(1H, s) | a) 2920, 1660, 1578, 1359, 1296, 1097. |
| 75 | 0.88(3H, t, J=6.7Hz), 2.15(6H, s), 2.35–2.55(1H, m), 2.6–2.8(1H, m), 3.75–3.90(1H, m), 4.0–4.1(1H, m), 5.86(1H, d, J=1.7Hz) | a) 2930, 1665, 1580, 1410, 1355, 1295, 1020. |
| 76 | 0.88(3H, t, J=6.8Hz), 2.13(6H, s), 2.35–2.55(1H, m), 2.6–2.8(1H, m), 3.75–3.85(1H, m), 3.9–4.0(1H, m), 5.84(1H, s) | a) 2915, 2860, 1665, 1575, 1355, 1290, 1093. |
| 77 | 0.88(3H, t, J=6.7Hz), 2.16(6H, s), 2.40–2.55(1H, m), 2.60–2.75(1H, m), 3.75–3.85(1H, m), 4.0–4.05(1H, m), 5.85(1H, d, J=2.0Hz) | a) 2920, 2855, 1670, 1577, 1358, 1295. |
| 78 | 0.87(3H, t, J=6.7Hz), 2.15(6H, s), 2.35–2.55(1H, m), 2.6–2.8(1H, m), 3.75–3.85(1H, m), 3.9–4.0(1H, m), 5.84(1H, s) | a) 2920, 2855, 1670, 1578, 1355. |
| 79 | 0.88(3H, t, J=6.7Hz), 2.16(6H, s), 2.40–2.52(1H, m), 2.60–2.75(1H, m), 3.75–3.85(1H, m), 4.0–4.05(1H, m), | a) 2920, 2855, 1655, 1577, 1350. |

-continued

| | | |
|---|---|---|
| | 5.85(1H, d, J=1.7Hz) | |
| 80 | 0.88(3H, t, J=6.6Hz), 2.16(6H, s), 2.39–2.50(1H, m), 2.64–2.75(1H, m), 3.76–3.85(1H, m), 3.95–4.00(1H, m), 5.84(1H, s) | a) 2920, 2850, 1665, 1576, 1355, 1290. |
| 81 | 0.88(3H, t, J=6.6Hz), 2.16(6H, s), 2.40–2.52(1H, m), 2.63–2.74(1H, m), 3.75–3.85(1H, m), 4.0–4.05(1H, m), 5.85(1H, d, J=2.0Hz) | a) 2920, 2860, 1663, 1577, 1356, 1290, 1090. |
| 82 | 0.88(3H, t, J=6.8Hz), 2.14(6H, s), 2.39–2.49(1H, m), 2.63–2.74(1H, m), 3.75–3.85(1H, m), 3.95–4.00(1H, m), 5.84(1H, s) | a) 2915, 2855, 1670, 1575, 1358, 1295, 1092. |
| 83 | 0.88(3H, t, J=6.7Hz), 2.16(6H, s), 2.40–2.52(1H, m), 2.63–2.75(1H, m), 3.75–3.85(1H, m), 4.00–4.05(1H, m), 5.85(1H, d, J=2.0Hz) | a) 2910, 2855, 1660, 1579, 1355, 1295, 1095. |
| 84 | 0.88(3H, t, J=6.6Hz), 2.14(6H, s), 2.39–2.49(1H, m), 2.63–2.74(1H, m), 3.75–3.85(1H, m), 3.95–4.00(1H, m), 5.84(1H, s) | a) 2920, 2850, 1670, 1575, 1355, 1290. |
| 85 | 35.5–36.5° C. | b) 1683, 1290, 1017, 705. |
| 86 | 71.5–72.5° C. | b) 1654, 1577, 1420, 1268, 712. |
| 87 | 40–41° C. | b) 1685, 1573, 1415, 1298, 1155, 710. |
| 88 | 59–60° C. | b) 1653, 1575, 1420, 1265, 1145, 710. |
| 89 | 45–46° C. | b) 1685, 1577, 1298, 1260, 1154, 710. |
| 90 | 76.5–77.5° C. | b) 1652, 1573, 1418, 1300, 712. |
| 91 | 42–44° C. | b) 1687, 1672, 1300, 1021. |
| 92 | 65–66° C. | b) 1650, 1577, 1142, 1020, |
| 93 | 52.5–53.5° C. | b) 1685, 1578, 1295, 1259. |
| 94 | 81–82° C. | b) 1652, 1577, 1420, 1142, 713. |
| 95 | 68–70° C. | b) 1690, 1578, 1300, 1260, 1159, 1020. |
| 96 | 63–64° C. | b) 1655, 1579, 1421, 1270, 1144, 713. |
| 97 | 57.5–58.5° C. | b) 1690, 1575, 1300, 1023, 710. |
| 98 | 84.5–85.5° C. | b) 1652, 1575, 1419, 1301, 1262, 1140, 709. |
| 99 | 53–56° C. | b) 1684, 1572, 1410, 709. |
| 100 | 73.5–75° C. | b) 1653, 1578, 1420, 1265, 1220, 710. |
| 101 | 4.07(1H, dq, J=1.7 and 7.0Hz), 5.65(1H, d, J=1.7Hz) | a) 2925, 2810, 1670, 1573, 1445, 1113. |
| 102 | 3.96(1H, dq, J=7.0Hz), 5.66(1H, s) | a) 2920, 2805, 1665, 1572, 1445, 1110. |
| 103 | 0.97(3H, t, J=7.3Hz), 2.16(6H, s), 3.6–3.75(1H, m), 4.0–4.1(1H, m), 5.63(1H, d, J=2.0Hz) | a) 2900, 1663, 1575. |
| 104 | 0.97(3H, t, J=7.3Hz), 2.22(6H, s), 3.55–3.70(1H, m), 3.9–4.0(1H, m), 5.68(1H, s). | a) 2860, 1660, 1410, 1300. |
| 105 | 0.89(3H, t, J=6.6Hz), 2.21(6H, s), 3.6–3.75(1H, m), 4.0–4.1(1H, m), 5.63(1H, d, J=2.0Hz) | a) 2910, 2860, 1665. |
| 106 | 0.88(3H, t, J=6.6Hz), 2.13(6H, s), 3.55–3.70(1H, m), 3.9–4.0(1H, m), 5.65(1H, S). | a) 2900, 2870, 1660, 1579. |
| 107 | 2.15(6H, s), 4.0–4.07(1H, m), 5.63(1H, d, J=1.7Hz) | a) 2910, 2855, 1670, 1577, 1300, 1020. |
| 108 | 2.13(6H, s), 3.94(1H, dd, J=3.7 and 9Hz), 5.65(1H, s) | a) 2930, 2860, 1670, 1580, 1300, 1020. |
| 109 | 77° C.–78° C. | b) 1675, 1586, 1512, 1253, 1021. |
| 110 | 55–56° C. | b) 1673, 1590, 1414, 1267, 1239, 1025, 800. |
| 111 | 63–64° C. | b) 1655, 1576, 1421, 1269, 719. |
| 112 | 73–74° C. | b) 1652, 1581, 1424, |

-continued

| | | |
|---|---|---|
| 113 | 65.5-66.5° C. | 1310, 1028, 715.<br>b) 1659, 1585, 1400,<br>1302, 1269, 1200,<br>1129, 703. |
| 114 | 0.85-0.9(3H, m), 2.16(4H, S), 2.17(2H, s),<br>3.0-3.75(1H, m), 3.9-4.0(0.67H, m),<br>4.0-4.1(0.33H, m), 5.59(0.33H, d,<br>J=2.0Hz), 5.62(0.67H, S) | a) 2840, 1655, 1408,<br>1350. |
| 115 | 0.88(3H, t, J=6.7Hz), 0.97(6H, t, J=7.1Hz),<br>3.65-3.8(1H, m), 3.95-4.05(1H, m),<br>5.89(1H, d, J=2.0Hz) | a) 2850, 1660. |
| 116 | 0.87(3H, t, J=6.7Hz), 0.95(6H, t, J=7.1Hz),<br>3.6-3.75(1H, m), 3.9-4.0(1H, m),<br>5.90(1H, m) | a) 2880, 1658. |
| 117 | 0.88(3H, t, J=6.6Hz), 1.06(3H, t, J=7.1Hz),<br>3.7-3.9(1H, m), 4.0-4.1(1H, m),<br>5.79(1H, d, J=1.7Hz) | a) 2860, 1665. |
| 118 | 0.88(3H, t, J=6.7Hz), 1.05(3H, t, J=7.1Hz),<br>3.65-3.80(1H, m), 3.95-4.0(1H, m),<br>5.81(1H, s) | a) 2900, 2850, 1663. |
| 119 | 0.85-0.9(3H, m), 2.6-2.8(2H, m),<br>3.75-4.1(2H, m), 5.88-5.86(1H, m) | a) 2850, 1658, 1350. |
| 120 | 2.83-2.88(4H, m), 3.66-3.78(4H, m),<br>3.94-3.99(0.5H, m), 3.99-4.03(0.5H, m)<br>5.85(0.5H, d, J=1.9Hz), 5.86(0.5H, s) | a) 2850, 1660. |
| 121 | 3.63-3.76(2H, m), 3.96-4.01(0.5H, m),<br>4.01-4.08(0.5H, m),<br>5.73(0.5H, d, J=1.7Hz), 5.76(0.5H, s) | a) 2850, 1660, 1577,<br>1403. |
| 122 | 2.17(3H, s), 5.90(0.5H, d, J=1.7Hz),<br>5.91(0.5H, s) | a) 2855, 1670, 1630. |
| 123 | 0.87(6H, d, J=6.6Hz), 0.95(3H, d, J=6.4Hz),<br>2.15(6H, s), 3.75-3.85(1H, m),<br>3.99-4.05(1H, m), 5.86(1H, d, J=2.0Hz) | a) 2855, 1660, 1578,<br>1358. |
| 124 | 2.15(6H, s), 3.75-3.85(1H, m),<br>4.0-4.05(1H, m), 5.14-5.26(2H, m)<br>5.85(1H, d, J=2.0Hz), 5.8-6.0(1H, m) | a) 2870, 1660, 1578,<br>1403, 1352. |
| 125 | 3.11-3.44(2H, m), 3.67-3.76(1H, m),<br>4.03-4.35(1H, m), 5.49(1H, d, J=2.0Hz) | a) 2770, 1660, 1577. |
| 126 | 2.15(6H, s), 3.75-3.85(1H, m),<br>4.0-4.05(1H, m), 5.86(1H, d, J=1.7Hz) | a) 2870, 1655, 1578,<br>1405, 1353. |
| 127 | 1.61(3H, d, J=6.8Hz), 2.16(6H, s)<br>3.8-3.9(1H, m), 3.95-4.15(1H, m)<br>5.88(1H, d, J=1.7Hz) | a) 2930, 1690, 1580,<br>1359, 1149. |
| 128 | 71.5-72.5° C. | b) 1659, 1573, 1415,<br>1283, 1100. |

| Compound No. | | M.P. or NMR (δ ppm) | IR cm$^{-1}$ |
|---|---|---|---|
| 130 | [structure] | CDCl$_3$; 2.03(6H, s),<br>4.45-4.6(4H, m),<br>5.64(1H, s) | CHCl$_3$; 2860, 1665,<br>1579, 1090 |
| 131 | [structure]<br>trans | CDCl$_3$; 2.12(6H, S),<br>4.52(2H, S),<br>5.80(1H, d, J=2.0Hz) | CHCl$_3$; 1665, 1590,<br>1405, 1090 |
| 132 | [structure] | CDCl$_3$; 2.13(6H, S),<br>3.3-4.5(4H, m),<br>3.55-3.8(5H, m),<br>5.72(1H, S) | CHCl$_3$; 2870, 1665,<br>1579, 1095 |

| | | | |
|---|---|---|---|
| 133 | 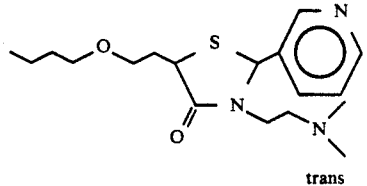 trans | CDCl₃; 2.15(6H, S), 4.1–4.2(1H, m), 5.83(1H, d, J=1.7Hz) | CHCl₃; 2850, 1662, 1578, 1100 |
| 134 | 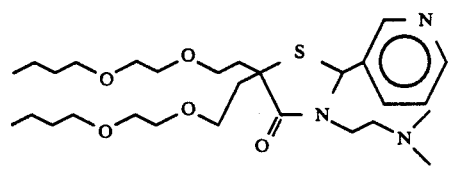 | CDCl₃; 0.86–0.95(6H, m), 1.30–1.63(8H, m), 2.13(6H, S), 5.73(1H, S) | CHCl₃; 2940, 2880, 1672, 1356, 1100 |
| 135 | 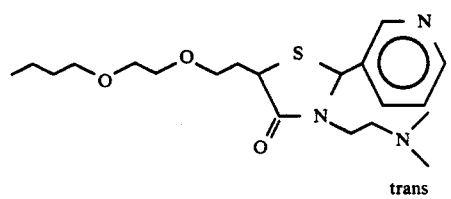 trans | CDCl₃; 2.15(6H, S), 4.12–4.17(1H, m), 5.83(1H, d, J=1.7Hz) | CHCl₃; 2860, 1662, 1572, 1350, 1095 |
| 136 | 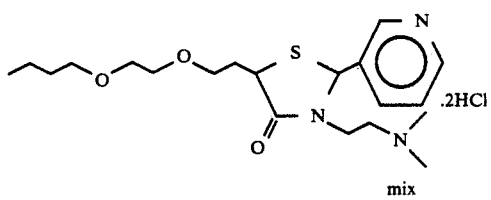 mix | DMSO; 0.85(3H, t, J=7.3Hz), 4.21–4.34(1H, m), 6.09(0.7H, d, J=1.5Hz), 6.13(0.3H, S) | KBr; 2870, 2680, 1678, 1418, 1110 |
| 137 | 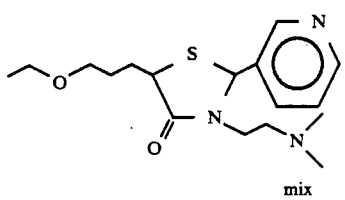 mix | CDCl₃; 2.14(1.8H, S), 2.15(1.2H, S), 4.01–4.08(1H, m), 5.85(1H, d, J=2Hz) | CHCl₃; 2940, 2860, 1670, 1598, 1590, 1380, 1360, 1300, 1105 |
| 138 | 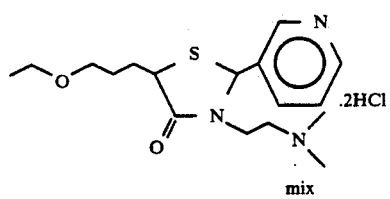 mix | m.p. 75–78° C. | KBr; 2930, 2870, 2700, 1675, 1414, 1108 |
| 139 | 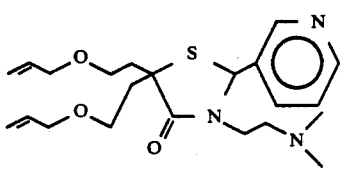 | CDCl₃; 2.12(6H, S), 5.12–5.33(4H, m), 5.72(1H, S), 5.85–6.00(2H, m) | CHCl₃; 1680, 1605, 1585, 1355, 1100, 990 |
| 140 | 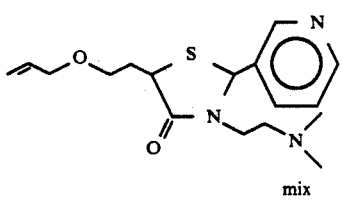 mix | CDCl₃; 2.13(1.2H, S), 2.15(4.8H, S), 4.13–4.18(1H, m), 5.16–5.32(2H, m), 5.79–5.82(2H, m) | CHCl₃; 1680, 1595, 1580, 1350, 1100 |

| | | | |
|---|---|---|---|
| 141 | 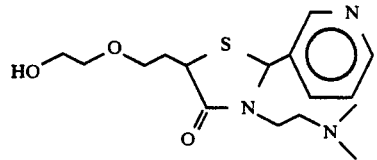 | CDCl₃; 2.13(3H, S), 2.15(3H, S), 4.09-4.19(1H, m), 5.85(0.5H, S), 5.88(0.5H, d, J=2Hz) | CHCl₃; 3300-3500 (br), 2825, 2775, 1670, 1597, 1590, 1360, 1290 |
| 142 | 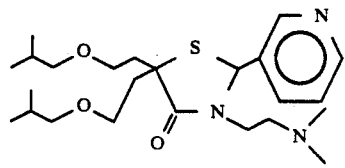 | CDCl₃; 0.92-0.87(12H, m), 2.13(6H, S), 5.73(1H, S) | CHCl₃; 2870, 1675, 1595, 1580, 1100 |
| 143 | 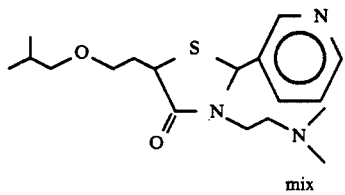 mix | CDCl₃; 0.89(6H, d, J=6.6Hz), 2.13(2.1H, S), 2.15(3.6H, S), 4.09-4.16(1H, m), 5.83(0.6H, d, J=2Hz), 5.84(0.4H, S) | CHCl₃; 2870, 1670, 1590, 1580, 1360, 1100 |
| 144 | 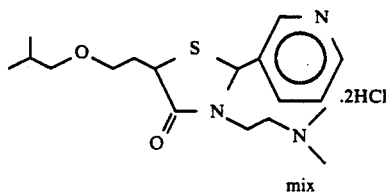 .2HCl mix | DMSO; 0.84(6H, d, J=6.8Hz), 4.31-4.34(1H, m), 6.09(0.8H, d, J=1.5Hz), 6.12(0.2H, S) | KBr; 2960, 2870, 2690, 1675, 1420, 1120 |
| 145 | 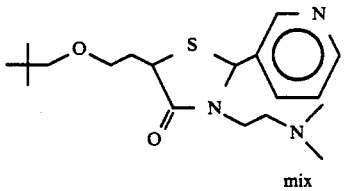 mix | CDCl₃; 1.17(9H, S), 2.14(3H, S), 2.15(3H, S), 4.07-4.15(1H, m), 5.82(1H, m) | CHCl₃; 2930, 2820, 2775, 1670, 1590, 1580, 1360, 1300, 1095 |
| 146 | 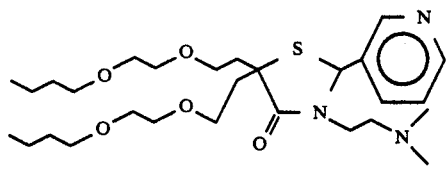 | CDCl₃; 0.87-0.95(6H, m), 2.12(6H, S), 3.19-3.24(4H, m), 5.74(1H, S) | CHCl₃; 2940, 2875, 1672, 1358, 1104 |
| 147 | 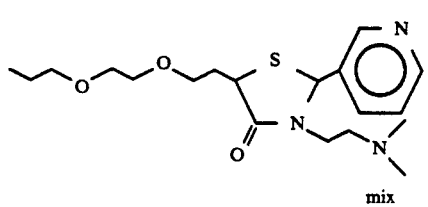 mix | CDCl₃; 0.90(3H, t, J=7Hz), 2.14(3H, S), 2.15(3H, S), 4.08-4.17(1H, m), 5.83-5.84(1H, m) | CHCl₃; 2925, 2870, 2825, 2775, 1670, 1590, 1580, 1360, 1300, 1100 |
| 148 | 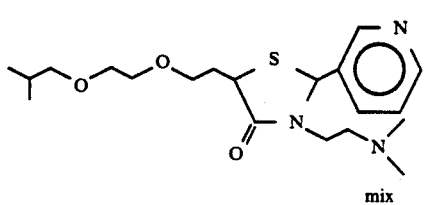 mix | DMSO-d₆; 0.83(3H, t, J=7.5Hz), 4.31-4.34(1H, m), 6.09(0.8H, d, J=1.5Hz), 6.12(0.2H, S) | KBr; 2875, 2690, 1678, 1408, 1114 |

| | | | |
|---|---|---|---|
| 149 | 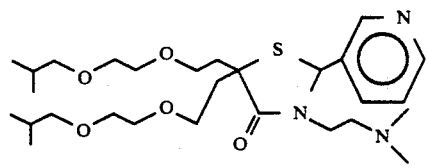 | CDCl₃; 0.86-0.92(12H, m), 1.2(6H, S), 3.19-3.24(4H, m), 5.74(1H, S) | CHCl₃; 2950, 2880, 1672, 1356, 1104 |
| 150 | 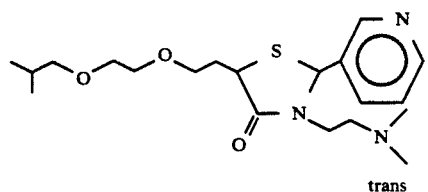 trans | CDCl₃; 0.88(6H, d, J=6.6Hz), 2.14(6H, S), 3.21(2H, d, J=6.8Hz), 4.13-4.16(1H, m), 5.83(1H, d, J=1.7Hz) | CHCl₃; 2940, 2863, 2775, 1668, 1592, 1578, 1358, 1096 |
| 151 | 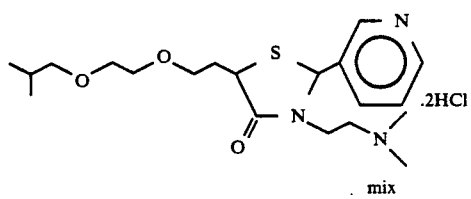 .2HCl mix | DMSO-d₆; 0.82(6H, d, J=6.6Hz), 4.30-4.33(1H, m), 6.11(0.8H, d, J=1.5Hz), 6.14(0.2H, S) | KBr; 2960, 2870, 2700, 1680, 1470, 1118 |
| 152 | 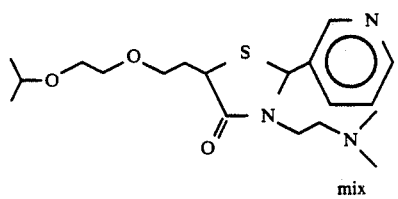 mix | CDCl₃; 1.15(6H, d, J=6Hz), 2.13(3H, S), 2.15(3H, S), 4.08-4.16(1H, m), 5.83-5.84(1H, m) | CHCl₃; 2870, 2825, 2775, 1670, 1590, 1580, 1125 |
| 153 | 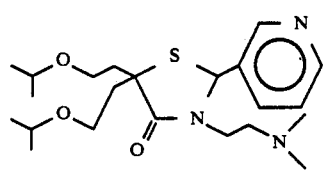 | CDCl₃; 1.12-1.72(12H, m), 3.54-3.78(7H, m), 5.72(1H, S) | CHCl₃; 2870, 2825, 2775, 1670, 1595, 1580, 1385, 1370, 1125, 1070 |
| 154 | 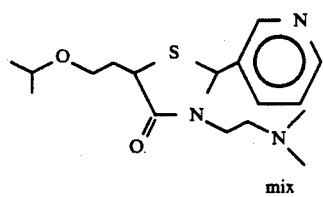 mix | CDCl₃; 1.13-1.59(1H, m), 3.74-3.86(1H, m), 4.07-4.16(1H, m), 5.83(1H, m) | CHCl₃; 2935, 2825, 2775, 1670, 1590, 1580, 1125 |
| 155 | 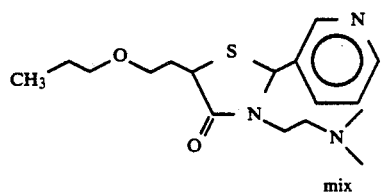 mix | CDCl₃; 2.13(3H, S), 2.15(3H, S), 3.38(3H, S), 4.08-4.13(1H, S), 5.34(1H, D, J=2Hz) | CHCl₃; 1670, 1590, 1580, 1355, 1090 |

-continued
| | | | |
|---|---|---|---|
| 156 | 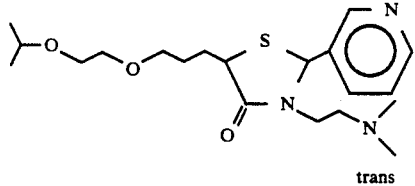 trans | CDCl₃; 1.16(6H, d, J=6.1Hz), 2.15(6H, S), 4.05–4.08(1H, m), 5.35(1H, d, J=2Hz) | CHCl₃; 2870, 2825, 2780, 1670, 1595, 1580, 1370, 1120 |
| 157 | 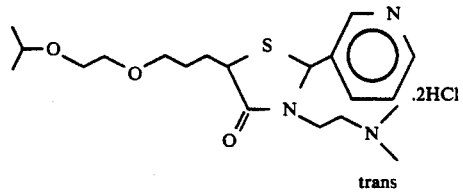 .2HCl trans | DMSO-d₆; 1.07(6H, d, J=6.1Hz), 4.33–4.36(1H, m), 6.12(1H, d, J=1.4Hz) | KBr; 2980, 2700, 1682, 1475, 1385, 1122 (KBr) |
| 158 | 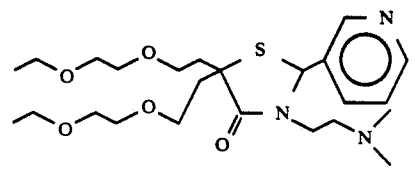 | CDCl₃; 1.19–1.25(6H, m), 2.14(6H, S), 5.77(1H, S) | CHCl₃; 2875, 1670, 1350, 1104 |
| 159 | 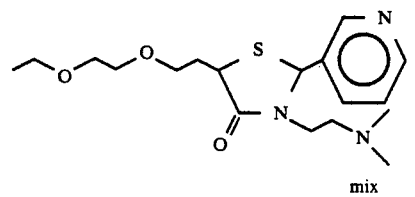 mix | CDCl₃; 1.20(3H, t, J=7Hz), 2.13(1H, S), 2.15(5H, S), 4.13–4.16(1H, m), 5.84(1H, d, J=2Hz) | CHCl₃; 2870, 2825, 2780, 1670, 1600, 1585, 1330, 1102 |
| 160 | 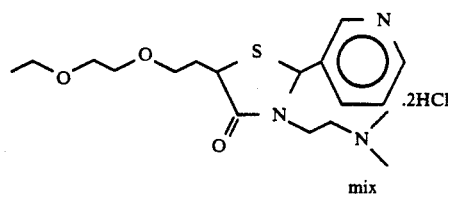 .2HCl mix | DMSO-d₆; 1.08(3H, t, J=7Hz), 4.31–4.34(1H, m), 6.01(0.8H, d, J=1.5Hz), 6.12(0.2H, S) | KBr; 2880, 2690, 1425, 1115 |
| 161 | 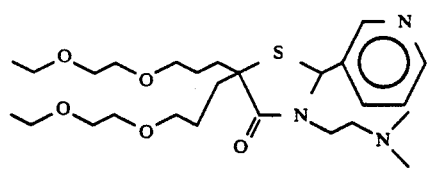 | CDCl₃; 1.19–1.25(6H, m), 2.13(6H, S), 5.77, (1H, S) | CHCl₃; 2870, 1666, 1348, 1100 |
| 162 | 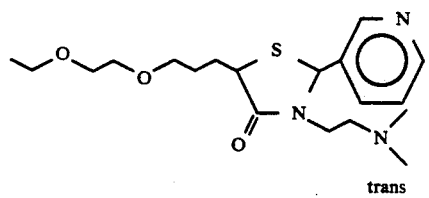 trans | CDCl₃; 1.22(3H, t, J=7.1Hz), 2.15(6H, S), 4.05–4.07(1H, m), 5.85(1H, d, J=1.7Hz) | CHCl₃; 2865, 2820, 2775, 1670, 1593, 1580, 1353, 1100 |
| 163 | 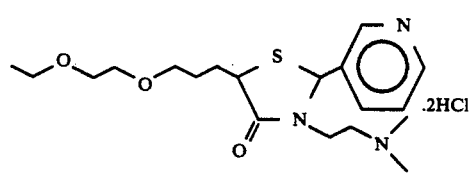 .2HCl trans | DMSO-d₆; 1.10(3H, t, J=7.1Hz), 4.33–4.37(1H, m), 6.12(1H, d, J=1.1Hz) | KBr; 2875, 2680, 1680, 1110 |

| | | | |
|---|---|---|---|
| 164 | 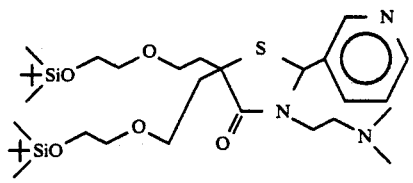 | CDCl₃; 0.05(6H, S), 0.08(6H, S), 0.88(9H, S), 0.90(9H, S), 2.15(6H, S), 5.72(1H, S) | CHCl₃; 2925, 2800, 1675, 1590, 1580, 1460, 1360, 1100, 830 |
| 165 | 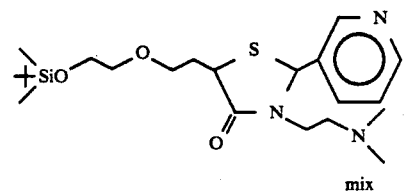 mix | CDCl₃; 0.05(6H, S), 0.88(7H, S), 2.14(2.4H, S), 2.15(3.6H, S), 4.09–4.16(1H, m), 5.83(0.6H, d, J=1.7Hz), 5.85(0.4H, S) | CHCl₃; 2925, 2860, 1675, 1590, 1580, 1360, 1095 |
| 166 | 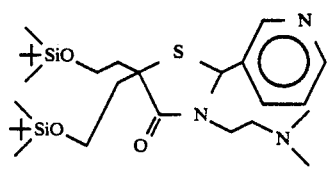 | CDCl₃; 0.05–0.07(12H, m), 0.88(9H, S), 0.90(9H, S), 2.13(6H, S), 5.73(1H, S) | CHCl₃; 2925, 2860, 1670, 1600, 1460, 1360, 1090, 830 |
| 167 | 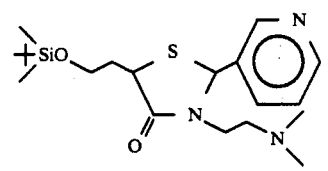 | CDCl₃; 0.05(6H, S), 0.89(9H, S), 2.14(2.4H, S), 2.15(3.6H, S), 4.08–4.16(1H, m), 5.83(0.6H, d, J=2Hz), 5.85(0.4H, S) | CHCl₃; 2925, 2860, 2825, 2780, 1670, 1590, 1580, 1460, 1360, 1100, 830 |
| 168 | 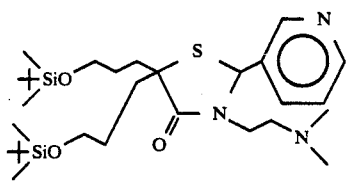 | CDCl₃; 0.04–0.07(12H, m), 0.88(9H, S), 0.90(9H, S), 2.13(6H, S), 5.81(1H, S) | CHCl₃; 2925, 2850, 2770, 1670, 1600, 1590, 1360, 1090, 830 |
| 169 | 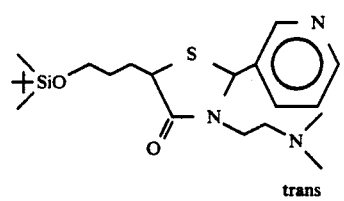 trans | CDCl₃; 0.06(6H, S), 0.81(9H, S), 2.15(6H, S), 3.67(2H, t, J=6Hz), 4.06–4.10(1H, m), 5.86(1H, d, J=2Hz) | CHCl₃; 1660, 1355, 1090, 830 |
| 170 | 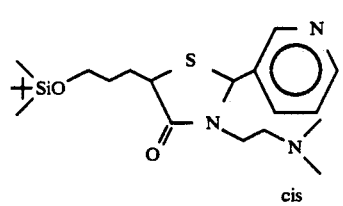 cis | m.p. 65.5–66° C. | nujol; 1660, 1090, 850, 775 |
| 171 | 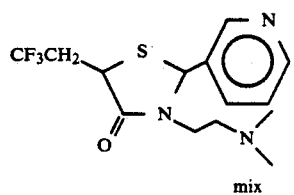 mix | CDCl₃; 2.13(3H, S), 2.16(3H, S), 2.63(1H, S), 2.67(1H, S), 4.15–4.26(1H, m), 5.85–5.91(1H, m) | CHCl₃; 1680, 1380, 1300, 1140 |

| | | | |
|---|---|---|---|
| 172 | 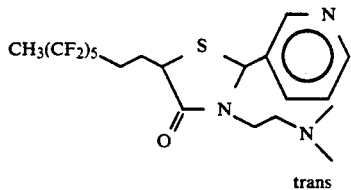 trans | m.p. 98.5–99.5° C. | nujol; 1670, 1590, 1580, 1140, 985 |
| 174 | 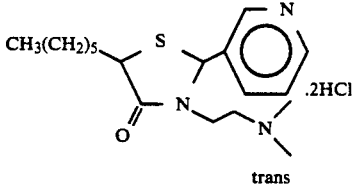 trans | 89–92° C. | KBr; 2920, 2850, 2680, 1676, 1462 |
| 175 | 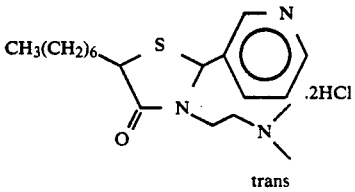 trans | 130–131.5° C. | KBr; 2930, 2860, 2680, 1680, 1470 |
| 176 | 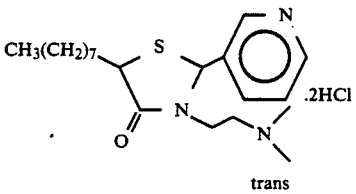 trans | 157–160° C. | KBr; 2925, 2860, 2670, 1680, 1464 |
| 177 | 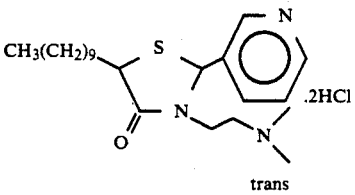 trans | 175–177° C. | KBr; 2925, 2850, 2670, 1678, 1466 |

EXAMPLE 29

Preparation of (+)-cis-3,5-dimethyl-2(3-pyridyl)-thiazolidin-4-one (compound No. 178)

A solution of N-nicotinylidenemethylamine (4.37 g, 36 mmol) in tetrahydrofuran (20 ml) was added dropwise to a solution of (−)-2-mercaptopropionic acid (3.86 g, 36 mmol) in tetrahydrofuran (40 ml) with stirring under a stream of nitrogen while cooling with ice. The reaction was allowed to proceed for 12 hours.

Then, the product mixture was dissolved in ethyl acetate (50 ml) and the solution was washed in turn with saturated aqueous NaHCO$_3$ (20 ml), water (20 ml), and aqueous NaCl, and dried. The solvent was removed under reduced pressure, giving a crude product in crystalline form (6.97 g), which was then washed with ether (10 ml) at 0° to 5° C. and, upon recrystallization from ether (10 ml) at −10° C., gave (+)-cis-3,5-dimethyl-2-(3-pyridyl)thiazolidin-4-one (3.77 g, 50% yield). m.p. 66.5°–68.5° C. $[\alpha]_D^{26} = +20.5°$ (C 0.44, CHCl$_3$).

EXAMPLE 30

Preparation of (-)-cis-3,5-dimethyl-2-(3-pyridyl)-thiazolidin-4-one (compound No. 179)

According to the procedure of Example 29, the title compound (3.24 g, 52% yield) was prepared from (+)-2-mercaptopropionic acid (3.19 g, 30 mmol) and N-nicotinylidenemethylamine (3.61 g, 30 mmol). m.p. 66.0°–68.5° C. $[\alpha]_D^{25} = -21.3°$ (C 3.28, CHCl$_3$).

EXAMPLE 31

Preparation of (-)-trans-3,5-dimethyl-2-(3-pyridyl)-thiazolidin-4-one (compound No. 180)

Titanium tetraisopropoxide (1.42 g, 5.0 mmol) was added to a solution of (-)-2-mercaptopropionic acid (0.53 g, 5.0 mmol) in dichloromethane (5 ml) with stirring at room temperature under a stream of nitrogen. Then, a solution of N-nicotinylidenemethylamine (0.60 g, 5.0 mmol) in dichloromethane (2 ml) was similarly added dropwise at room temperature. The reaction was allowed to proceed for 5 hours. The product mixture, after addition of water, was celite-filtered using dichloromethane (20 ml) as washing liquid. The resulting organic layer was washed with water (10 ml) and then with aqueous NaCl, and dried. The solvent was removed under reduced pressure, leaving a crude product (0.44 g). Purification thereof by silica gel flash chromatography (hexane: 2-propanol=4:1) gave (-)-trans-3,5-dimethyl-2-(3-pyridyl)thiazolidin-4-one (54 mg) in oily form. $n_D^{27}=1.6043$. $[\alpha]_D^{25}= -132.5°$ (C 0.28, CHCl$_3$).

EXAMPLE 32

Preparation of (+)-trans-3,5-dimethyl-2-(3-pyridyl)-thiazolidin-4-one (compound No. 181)

According to the procedure of Example 31, the title compound (49 mg) in oily form was prepared from (+)-2-mercaptopropionic acid (0.53 g, 5.0 mmol), titanium tetraisopropoxide (1.42 g, 5.0 mmol), and N-nicotinylidenemethylamine (0.60 g, 5.0 mmol). $n_D^{26}=1.6039$ $[\alpha]_D^{25}= +130.8°$ (C 0.34, CHCl$_3$).

EXAMPLE 33

Preparation of 3,5-dimethyl-2-(3-pyridyl)thiazolidin-4-one hydrochloride (compound No. 182)

Conc. aqueous HCl (4.75 g, 45.6 mmol) was added dropwise to a solution of cis-3,5-dimethyl-2-(3-pyridyl)-thiazolidin-4-one (10 g, 48 mmol) from Example 2 in ethanol (50 ml) at room temperature. Then the mixture was cooled to 0° C., and the precipitated crystals were filtered and the title compound (9.621 g, 86.28 yield) was obtained. m.p. 190°–193° C.

EXAMPLE 34

Preparation of half fumaric acid addition salt of 3,5-dimethyl-2-(3-pyridyl)thiazolidin-4-one (compound No. 183)

cis-3,5-Dimethyl-2-(3-pyridyl)thiazolidin-4-one (20 g, 96 mmol) from Example 2 and fumaric acid (5.58 g, 48 mmol) were dissolved in ethanol (100 ml) and the solution was stirred for 1 hour at room temperature. Then the ethanol was removed under reduced pressure. The residue, upon recrystallization from ethyl acetate, gave the title compound (15.88 g, 62% yield). m.p. 140°–143° C.

What is claimed is:

1. A thiazolidin-4-one derivative represented by the following formula (I) or a pharmaceutically acceptable salt thereof:

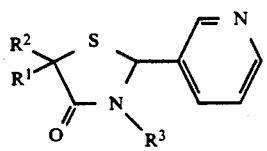

(I)

wherein $R^1$ is n-heptyl, n-octyl, n-nonyl, n-decyl, n-undecyl, n-dodecyl, $C_2$–$C_8$ alkenyl, $C_3$–$C_8$ cycloalkyl, $C_1$–$C_8$ alkynyl, $C_1$–$C_8$ haloalkyl or a residue represented by the formula:

wherein B is a single bond or $C_1$–$C_6$ alkylene, $R^5$ is hydrogen, $C_1$–$C_6$ alkyl, $C_2$–$C_8$ alkenyl, $C_3$–$C_8$ cycloalkyl, t-butyldimethyl silyl, or phenyl, n and n' each are an integer of 2 to 4, m is an integer of 1 to 3, and m' is an integer of 0 to 2; and $R^2$ is hydrogen or a residue represented by the formula

wherein B is a single bond or $C_1$–$C_6$ alkylene, $R^5$ is hydrogen, $C_1$–$C_6$ alkyl, $C_2$–$C_8$ alkenyl, $C_3$–$C_8$ cycloalkyl, t-butyldimethyl silyl, or phenyl, n and n' each are an integer of 2 to 4, m is an integer of 1 to 3, and m' is an integer of 0 to 2; and $R^3$ is a residue represented by the formula

wherein F is $C_2$–$C_3$ alkylene and $R^9$ is an amino group represented by the formula

wherein $R^{10}$ and $R^{11}$ are independently hydrogen or $C_1$–$C_4$ alkyl.

2. A compound according to claim 1, wherein $R^1$ is n-heptyl, n-octyl, n-nonyl, n-decyl, n-undecyl, n-dodecyl, or a residue represented by the formula

wherein B is a single bond or $C_1$–$C_6$ alkylene, $R^5$ is hydrogen, $C_1$–$C_6$ alkyl, $C_2$–$C_8$ alkenyl, $C_3$–$C_8$ cycloalkyl, substituted silyl, or substituted or unsubstituted aryl, n and n' each are an integer of 2 to 4, m is an integer of 1 to 3, and m' is an integer of 0 to 2, and $R^2$ is hydrogen.

3. A compound according to claim 1, wherein $R^1$ is a residue represented by the formula:

wherein B is a single bond or $C_1$–$C_6$ alkylene, $R^5$ is hydrogen, $C_1$–$C_6$ alkyl, $C_2$–$C_8$ alkenyl, $C_3$–$C_8$ cycloalkyl, substituted silyl, or substituted or unsubstituted aryl, n and n' each are an integer of 2 to 4, m is an integer of 1 to 3, and m' is an integer of 0 to 2; and $R^2$ is hydrogen.

4. A compound according to claim 1, wherein $R^1$ is n-heptyl, n-octyl, n-nonyl, n-decyl, n-undecyl, n-dodecyl, or a residue represented by the formula:

wherein B is a single bond or $C_1$–$C_6$ alkylene, $R^5$ is hydrogen, $C_1$–$C_6$ alkyl, $C_2$–$C_8$ alkenyl, $C_3$–$C_8$ cycloalkyl, substituted silyl, or substituted or unsubstituted aryl, n and n' each are an integer of 2 to 4, m is an integer of 1 to 3, and m' is an integer of 0 to 2; $R^2$ is hydrogen, and $R^3$ is a residue represented by the formula:

$-F-R^9$ wherein F is ethylene and $R^9$ is an amino group represented by the formula:

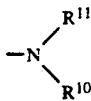

wherein $R^{10}$ and $R^{11}$ are independently hydrogen, methyl or ethyl.

5. A compound according to claim 1, wherein $R^1$ is a residue represented by the formula

wherein B is a single bond or $C_1-C_6$ alkylene, $R^5$ is hydrogen, $C_1-C_6$ alkyl, $C_2-C_8$ alkenyl, $C_3-C_8$ cycloalkyl, substituted silyl, or substituted or unsubstituted aryl, and n and n' each are an integer of 2 to 4, m is an integer of 1 to 3, and m' is an integer of 0 to 2; $R^2$ is hydrogen, and $R^3$ is a residue represented by the formula:

$-F-R^9$ wherein F is ethylene and $R^9$ is an amino group represented by the formula

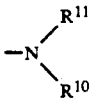

wherein $R^{10}$ and $R^{11}$ are independently hydrogen, methyl or ethyl.

6. A pharmaceutical composition for treatment of a disease caused by the platelet activating factor, which comprises as an active ingredient a pharmaceutically effective amount of a compound represented by the formula

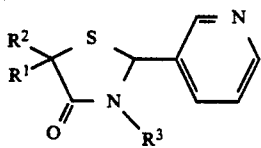

(I)

wherein $R^1$ is n-heptyl, n-octyl, n-noneyl, n-decyl, n-undecyl, n-dodecyl, $C_2-C_8$ alkenyl, $C_3-C_8$ cycloalkyl, $C_1-C_8$ alkynyl, $C_1-C_6$ haloalkyl or a residue represented by the formula

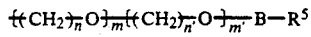

wherein B is a single bond or $C_1-C_6$ alkylene, $R^5$ is hydrogen, $C_1-C_6$ alkyl, $C_2-C_8$ alkenyl, $C_3-C_8$ cycloalkyl, t-butyldimethyl silyl, or phenyl, n and n' each are an integer of 2 to 4, m is an integer of 1 to 3, and m' is an integer of 0 to 2; and $R^2$ is hydrogen or a residue represented by the formula

wherein B is a single bond or $C_1-C_6$ alkylene, $R^5$ is hydrogen, $C_1-C_6$ alkyl, $C_2-C_8$ alkenyl, $C_3-C_8$ cycloalkyl, t-butyldimethyl silyl, or phenyl, n and n' each are an integer of 2 to 4, m is an integer of 1 to 3, and m' is an integer of 0 to 2; and $R^3$ is a residue represented by the formula

wherein F is $C_2-C_3$ alkylene and $R^9$ is an amino group represented by the formula:

wherein $R^{10}$ and $R^{11}$ are independently hydrogen or $C_1-C_4$ alkyl; and a pharmaceutically acceptable inert carrier or diluent.

7. A pharmaceutical composition according to claim 6 wherein the disease is inflammation, circulatory disease, gastrointestinal ulceration or allergic disease.

8. A pharmaceutical composition according to claim 7 wherein the circulatory disease is DIC (disseminated intravascular coagulation) or endotoxin shock.

9. A pharmaceutical composition according to claim 7 wherein the allergic disease is asthma.

10. A pharmaceutical composition according to claim 7 wherein the gastrointestinal ulceration ia gastric ulcer.

11. A pharmaceutical composition according to claim 7 wherein the inflammation is nephritis or rheumatism.

12. A method for treatment of a disease caused by the platelet activating factor, which comprises administering to a patient a pharmaceutically effective amount of a compound represented by the formula:

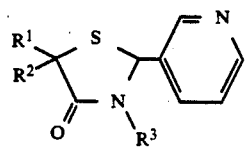

wherein $R^1$, $R^2$ and $R^3$ are as defined in claim 6 or a pharmaceutically acceptable salt thereof.

* * * * *

UNITED STATES PATENT AND TRADEMARK OFFICE
CERTIFICATE OF CORRECTION

PATENT NO. : 5,106,860
DATED : April 21, 1992
INVENTOR(S) : Masao ENOMOTO et al

It is certified that error appears in the above-identified patent and that said Letters Patent is hereby corrected as shown below:

On title page, item [73], should read:

--SUMITOMO PHARMACEUTICALS COMPANY, LIMITED--

Signed and Sealed this

Twenty-third Day of February, 1999

Attest:

Q. TODD DICKINSON

*Attesting Officer*  *Acting Commissioner of Patents and Trademarks*